US009859504B2

(12) United States Patent
Bilyk et al.

(10) Patent No.: US 9,859,504 B2
(45) Date of Patent: Jan. 2, 2018

(54) DIAMINE COMPOUNDS FOR PHOSPHORESCENT DIAZABOROLE METAL COMPLEXES AND ELECTROLUMINESCENT DEVICES

(71) Applicant: Commonwealth Scientific and Industrial Research Organisation, Campbell, Australian Capital Territory (AU)

(72) Inventors: Alexander Bilyk, Mount Waverley (AU); Mark Bown, Notting Hill (AU); Anthony Wilson, Altona Meadows (AU); Kazunori Ueno, Glen Waverley (AU)

( * ) Notice: Subject to any disclaimer, the term of this patent is extended or adjusted under 35 U.S.C. 154(b) by 337 days.

(21) Appl. No.: 14/673,232

(22) Filed: Mar. 30, 2015

(65) Prior Publication Data
US 2015/0280137 A1 Oct. 1, 2015

(30) Foreign Application Priority Data
Mar. 31, 2014 (AU) ................. 2014901153

(51) Int. Cl.
| H01L 51/00 | (2006.01) |
|---|---|
| C07D 409/12 | (2006.01) |
| C07F 5/02 | (2006.01) |
| C07F 15/00 | (2006.01) |
| C07D 333/34 | (2006.01) |
| H01L 51/50 | (2006.01) |
| H01L 51/52 | (2006.01) |

(52) U.S. Cl.
CPC ........ *H01L 51/0068* (2013.01); *C07D 333/34* (2013.01); *C07D 409/12* (2013.01); *C07F 5/022* (2013.01); *C07F 15/0033* (2013.01); *H01L 51/5012* (2013.01); *H01L 51/5056* (2013.01); *H01L 51/5072* (2013.01); *H01L 51/5206* (2013.01); *H01L 51/5221* (2013.01)

(58) Field of Classification Search
CPC ...... C07C 211/51; C07F 15/004; C09K 11/06
See application file for complete search history.

(56) References Cited

U.S. PATENT DOCUMENTS

| 8,617,723 | B2 | 12/2013 | Stoessel et al. | |
|---|---|---|---|---|
| 2003/0178561 | A1* | 9/2003 | Neda ................. | G01N 21/65 250/281 |
| 2005/0069729 | A1 | 3/2005 | Ueda et al. | |
| 2006/0175958 | A1 | 8/2006 | Gerhard et al. | |
| 2006/0208221 | A1 | 9/2006 | Gerhard et al. | |
| 2007/0176147 | A1 | 8/2007 | Buesing et al. | |
| 2009/0134384 | A1 | 5/2009 | Stoessel et al. | |
| 2009/0167166 | A1 | 7/2009 | Bach et al. | |
| 2009/0302742 | A1 | 12/2009 | Komori et al. | |
| 2009/0302752 | A1 | 12/2009 | Parham et al. | |
| 2010/0187977 | A1 | 7/2010 | Kai et al. | |
| 2010/0244009 | A1 | 9/2010 | Parham et al. | |
| 2010/0295032 | A1 | 11/2010 | Kwong et al. | |
| 2010/0331506 | A1 | 12/2010 | Fortte et al. | |
| 2012/0004407 | A1* | 1/2012 | Stoessel ................. | C07F 5/022 544/225 |

FOREIGN PATENT DOCUMENTS

| EP | 0652273 | 11/1993 |
|---|---|---|
| EP | 1191612 | 3/2002 |
| EP | 1191613 | 3/2002 |
| EP | 1191614 | 3/2002 |
| EP | 1205527 | 5/2002 |
| EP | 1617710 | 1/2006 |
| EP | 1617711 | 1/2006 |
| EP | 1731584 | 12/2006 |
| JP | 2004288381 | 10/2004 |
| JP | 2005347160 | 12/2005 |
| SU | 1085204 | 8/1982 |
| WO | 0070655 | 11/2000 |
| WO | 0141512 | 6/2001 |
| WO | 0202714 | 1/2002 |
| WO | 0215645 | 2/2002 |
| WO | 2004013080 | 2/2004 |
| WO | 2006005627 | 1/2006 |
| WO | 2011134013 | 11/2011 |
| WO | 2014006913 | 1/2014 |
| WO | 2014044347 | 3/2014 |

OTHER PUBLICATIONS

Atzrodt et a.l (2000) "Nucleophilic Substitution of 4H-Imidazoles—A Key Step in the Synthesis of Fused Imidazoles and New Chromophores," European Journal of Organic Chemistry; 8:1661-1668.

Nemeryuk et al. (1989) "Derivatives of 6,7,8,9-tetrahydrodipyrimido(4,5-b)(4',5'e) (1,4)thiazine. Synthesis and structure," Chimija Geterocikli Gbp Eeskich Soedinenij=Chemistry of Heterocyclic Compounds; 2:258-264.

Salunke et al. (2012) "Structure-Activity Relationships in Human Toll-like Receptor 8-Active 2,3-Diamino-furo[2,3-c] pyridines," Journal of Medicinal Chemistry; 55(18):8137-8151.

Arnold et al. (2008) "Direct vapor jet printing of three color segment organic light emitting devices for white light illumination," Appl. Phys. Lett.; 92:053301.

Baldo (1999) "Very high-efficiency green organic light-emitting devices based on electrophosphorescence," Appl. Phys. Lett.; 75:4-6.

* cited by examiner

*Primary Examiner* — Kuo-Liang Peng
(74) *Attorney, Agent, or Firm* — Rudy J. Ng; Glenn J. Foulds; Bozicevic, Field & Francis LLP

(57) ABSTRACT

The present disclosure generally relates to diamine compounds, which may be used as precursors in preparing diazaborole compounds and phosphorescent diazaborole metal complexes. The present disclosure also relates to diazaborole compounds, diazaborole metal complexes, and electroluminescent emission materials and electronic devices thereof. The present disclosure further relates to processes for preparing the diamine compounds and diazaborole metal complexes.

20 Claims, No Drawings

DIAMINE COMPOUNDS FOR PHOSPHORESCENT DIAZABOROLE METAL COMPLEXES AND ELECTROLUMINESCENT DEVICES

CROSS-REFERENCE TO RELATED APPLICATION

This application claims priority benefit of Australian application no. AU 2014901153, filed Mar. 31, 2014, which application is incorporated herein by reference in its entirety.

FIELD

The present disclosure generally relates to diamine compounds, which may be used as precursors in preparing diazaborole compounds and phosphorescent diazaborole metal complexes. The present disclosure also relates to diazaborole compounds, diazaborole metal complexes, and electroluminescent emission materials and electronic devices thereof. The present disclosure further relates to processes for preparing the diamine compounds and diazaborole metal complexes.

BACKGROUND

Organic electroluminescent devices (OLEDs) comprising organic semiconductors as functional emission materials are well known. An organic electroluminescent device is generally comprised of a pair of electrodes forming an anode and a cathode, and one layer or multiple layers comprising a hole transporting layer, emission layer (with an emissive material) and electron transporting layer. A voltage differential applied across the cathode and anode inject holes and electrons into the organic layer(s), which results in the formation of excitons within the emission material. The emission material then emits light when the excitons transition to the ground state.

New and improved phosphorescent materials for this type of application are continually being sought, since the luminous efficiency of OLEDs may potentially be improved by up to a factor of four when phosphorescent emitters are used in place of fluorescent emitters.

Organometallic complexes are increasingly being used as phosphorescent (triplet) emission materials in OLEDs (M. A. Baldo et al., Appl. Phys. Lett. 1999, 75, 4-6). Organometallic complexes can possess strong intersystem crossing from the singlet to the triplet state and is partly responsible for their success, for application in OLEDs. Metal complexes can also used in other functions in OLEDs, such as matric materials, electron-transport materials, hole-blocking materials or as dopants for use in one or more layers of such devices.

Improvements are still required in the physical properties of phosphorescent OLEDs, for example in respect of the stability of the metal complexes, efficiency, operating voltage and lifetime for use of triplet emitters in high-quality and long-lived electroluminescent devices. Improvements are sought for red-, green- and blue-phosphorescent metal complexes used in OLEDs, and particularly for blue-phosphorescent metal complexes. In working towards this, the emission wavelength ($\lambda_{em}$), lifetimes ($\tau$) and quantum yields ($\varphi_P$) are important considerations when searching for suitable phosphorescent materials.

Consequently, there is a need to identify compounds that can act as ligands for facilitating stability in phosphorescent metal complexes. There is also a need to identify novel metal complexes that can be used in OLEDs as emission materials or other functional materials such as matrix materials, hole-blocking materials and electron-transport materials.

SUMMARY

The present disclosure provides diamine compounds, which can be used as precursors in preparing phosphorescent metal complexes. The diamine compounds can act as chelating ligands in diazaborole metal complexes. The diamine compounds may facilitate tunability and provide stability in diazaborole metal complexes, or at least provide alternative or improved phosphorescent compounds and emission materials for OLEDs.

In one aspect, there is provided a compound of Formula 1 or Formula 2:

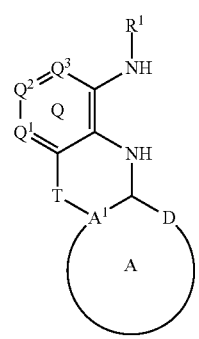

Formula 1

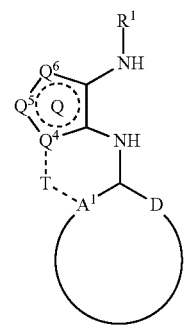

Formula 2 wherein $R^1$ is selected from $C_{1-20}$alkyl, $C_{2-20}$alkenyl, $C_{2-20}$alkynyl, and a 5 or 6 membered aryl or heteroaryl, each of which is optionally substituted with one or more substituents independently selected from halo, CN, $NO_2$, $C(O)R^2$, $OR^2$, $OS(O)_2R^2$, $NR^2R^3$, $SR^2$, aryl and heteroaryl; wherein $R^2$ and $R^3$ are each independently selected from hydrogen and $C_{1-6}$alkyl;

Q is an optionally substituted, optionally fused 5 or 6 membered heterocyclic ring, wherein the dashed circle indicates the optional location of up to two optional double bonds in the ring; and $Q^1$, $Q^2$ and $Q^3$, are each independently selected from $CR^4$ or N; wherein at least one of $Q^1$, $Q^2$ and $Q^3$ is N; and $R^4$ is independently selected from hydrogen, halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, optionally substituted 5 or 6 membered aryl or heteroaryl, and optionally two $R^4$ substituents from adjacent ring atoms are joined together to form an optionally substituted 5 or 6 membered aryl or heteroaryl ring; wherein $R^2$ and $R^3$ are defined as above;

$Q^4$, $Q^5$ and $Q^6$, are each independently selected from N, S, O, $CR^4$ and $NR^5$, wherein at least one of $Q^4$, $Q^5$ and $Q^6$ is selected from N, S, O and $NR^5$; wherein $R^4$ is defined as above and $R^5$ is defined according to $R^1$ above; with the proviso that when T is present then $Q^4$ is selected from C-T and N-T, and when T is absent Q is not a furo[2,3-C]pyridine group;

T is a tether group between rings Q and A of 1 to 3 atoms in length linked together in a linear chain, wherein the dashed lines between $Q^4$ atom and A ring indicates T is an optional group, and wherein T is selected from C, N, O, S, Si and B, each of which is optionally substituted with one or more substituents independently selected from hydrogen, halo, CN, $NO_2$, =O, $C(O)R^2$, $OR^2$, $OS(O)_2R^2$, $NR^2R^3$, $SR^2$, optionally substituted $C_{1-10}$alkyl, optionally substituted $C_{2-10}$alkenyl, optionally substituted $C_{2-10}$alkynyl and optionally substituted 5 or 6 membered aryl or heteroaryl, and optionally fused with a 3-6 membered carbocycle or heterocycle; and wherein $R^2$ and $R^3$ are each independently defined as above, A is a monocyclic or bicyclic 5 or 6 membered heterocyclic ring containing a donor atom D and a ring atom $A^1$, and optionally having 1 or 2 additional ring heteroatoms selected from O, S and N, wherein the heterocyclic ring is optionally substituted with 1 to 3 substituents independently selected from hydrogen, halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, and optionally substituted 5 or 6 membered aryl or heteroaryl; wherein $R^2$ and $R^3$ are each independently defined as above;

$A^1$ is selected from C, O, S, N, $CR^8$, $C(R^8)_2$ and $NR^9$; wherein each $R^8$ is independently selected from hydrogen, halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, optionally substituted 5 or 6 membered aryl or heteroaryl; $R^9$ is selected from hydrogen, $C_{1-20}$alkyl, $C_{2-20}$alkenyl, $C_{2-20}$alkynyl, and a 5 or 6 membered aryl or heteroaryl, each of which can be optionally substituted with one or more substituents independently selected from halo, CN, $NO_2$, $C(O)R^2$, $OR^2$, $OS(O)_2R^2$, $NR^2R^3$, $SR^2$, aryl and heteroaryl; and wherein $R^2$ and $R^3$ are defined as above;

D is a donor atom selected from N, O, S, P, Se and Te.

In one embodiment, $R^1$ is selected from optionally substituted $C_{1-20}$alkyl and optionally substituted monocyclic 5 or 6 membered aryl or heteroaryl. In another embodiment, $R^1$ is selected from optionally substituted $C_{1-10}$alkyl.

In one embodiment, the Q ring is an optionally substituted monocyclic 5 or 6 membered heterocyclic ring. In another embodiment, the Q ring is an optionally substituted monocyclic 5 or 6 membered heteroaryl ring, for example optionally substituted pyridine or thiophene. In another embodiment, the Q ring is optionally substituted with a group selected from optionally substituted $C_{1-20}$alkyl and optionally substituted 5 or 6 membered aryl or heteroaryl. In another embodiment, the Q ring is optionally fused with a group selected from optionally substituted monocyclic 5 or 6 membered aryl or heteroaryl, for example optionally substituted benzene and pyridine.

In some embodiments, when T is absent, the Q ring is not fused to a pyridine ring. In some embodiments, the Q ring is not part of a furo[2,3-C]pyridine fused ring system.

In one embodiment, T is a tether group provided by a linear chain of 1 to 3 atoms in length independently selected from $-N(R^7)-$, $-N(R^7)-C(=O)-$, $-O-$, $-O-C(=O)-$, $-C(=O)-$, $-S-$, $-S(=O)-$, $-S(=O)_2-$, $C_{1-3}$alkyl and $C_{2-3}$alkenyl; wherein the $C_{1-3}$alkyl and $C_{2-3}$alkenyl are each optionally interrupted by a group selected from $-N(R^7)-$, $-N(R^7)-C(=O)-$, $-O-$, $-O-C(=O)-$, $-C(=O)-$, $-S-$, $-S(=O)-$ and $S(=O)_2$, and optionally substituted with one or more substituents independently selected from halo, CN, $NO_2$, $C(O)R^2$, $OR^2$, $OS(O)_2R^2$, $NR^2R^3$, $SR^2$, $C_{1-10}$alkyl, $C_{2-10}$alkenyl, $C_{2-10}$alkynyl, $C_{1-10}$alkylhalo, $C_{2-10}$alkenylhalo and $C_{2-10}$alkynylhalo, and optionally fused with a 3-6 membered carbocycle or heterocycle. $R^7$ can be selected from hydrogen and $C_{1-10}$alkyl. In another embodiment, T is an optionally substituted, optionally fused $C_{1-3}$ group, for example an optionally substituted $C_{1-3}$alkyl or $C_{2-3}$alkenyl. In another embodiment, the optional substitution on the tether group T may be independently selected from optionally substituted $C_{1-6}$alkyl, for example optionally substituted methyl, ethyl or propyl.

In one embodiment, A is an optionally substituted monocyclic or bicyclic 5 or 6 membered heterocyclic ring containing at least one unsaturated bond. In another embodiment, A is an optionally substituted monocyclic or bicyclic 5 or 6 membered heteroaryl ring. In another embodiment, D is selected from N, for example wherein A is an optionally substituted pyridine group. In another embodiment, $A^1$ is selected from C or $CR^8$.

In another aspect, there is provided a compound of Formula 3 or Formula 4:

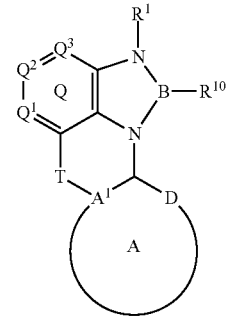

Formula 3

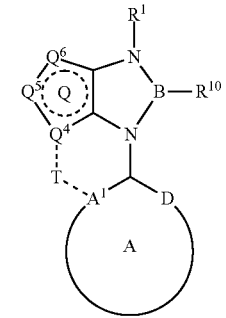

Formula 4 wherein $R^1$ is selected from $C_{1-20}$alkyl, $C_{2-20}$alkenyl, $C_{2-20}$alkynyl, and a 5 or 6 membered aryl or heteroaryl, each of which is optionally substituted with one or more substituents independently selected from halo, CN, $NO_2$, $C(O)R^2$, $OR^2$, $OS(O)_2R^2$, $NR^2R^3$, $SR^2$, aryl and heteroaryl; wherein $R^2$ and $R^3$ are each independently selected from hydrogen and $C_{1-6}$alkyl;

Q is an optionally substituted, optionally fused 5 or 6 membered heterocyclic ring, wherein the dashed circle indicates the optional location of up to two optional double bonds in the ring; and $Q^1$, $Q^2$ and $Q^3$, are each independently selected from $CR^4$ or N; wherein at least one of $Q^1$, $Q^2$ and $Q^3$ is N; and $R^4$ is independently selected from hydrogen, halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, optionally substituted 5 or 6 membered aryl or heteroaryl, and optionally two $R^4$ substituents from adjacent ring atoms are joined together to form an optionally substituted 5 or 6 membered aryl or heteroaryl ring; wherein $R^2$ and $R^3$ are defined as above;

$Q^4$, $Q^5$ and $Q^6$, are each independently selected from N, S, O, $CR^4$ and $NR^5$, wherein at least one of $Q^4$, $Q^5$ and $Q^6$ is selected from N, S, O and $NR^5$; wherein $R^4$ is defined as above and $R^5$ is defined according to $R^1$ above; with the proviso that when T is present then $Q^4$ is selected from C-T and N-T, and when T is absent Q is not a furo[2,3-C]pyridine group;

T is a tether group between rings Q and A of 1 to 3 atoms linked together in a linear chain, wherein the dashed lines between $Q^4$ atom and A ring indicates T is an optional group, and wherein T is selected from C, N, O, S, Si and B, each of which is optionally substituted with one or more substituents independently selected from hydrogen, halo, CN, $NO_2$, =O, $C(O)R^2$, $OR^2$, $OS(O)_2R^2$, $NR^2R^3$, $SR^2$, optionally substituted $C_{1-10}$alkyl, optionally substituted $C_{2-10}$alkenyl, optionally substituted $C_{2-10}$alkynyl and optionally substituted 5 or 6 membered aryl or heteroaryl, and optionally fused with a 3-6 membered carbocycle or heterocycle; and wherein $R^2$ and $R^3$ are each independently defined as above;

A is a monocyclic or bicyclic 5 or 6 membered heterocyclic ring containing a donor atom D and a ring atom $A^1$, and optionally having 1 or 2 additional ring heteroatoms selected from O, S and N, wherein the heterocyclic ring is optionally substituted with 1 to 3 substituents independently selected from halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, and optionally substituted 5 or 6 membered aryl or heteroaryl; wherein $R^2$ and $R^3$ are each independently defined as above;

$A^1$ is selected from C, O, S, N, $CR^8$, $C(R^8)_2$ and $NR^9$; wherein each $R^8$ is independently selected from hydrogen, halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, optionally substituted 5 or 6 membered aryl or heteroaryl; $R^9$ is selected from hydrogen, $C_{1-20}$alkyl, $C_{2-20}$alkenyl, $C_{2-20}$alkynyl, and a 5 or 6 membered aryl or heteroaryl, each of which can be optionally substituted with one or more substituents independently selected from halo, CN, $NO_2$, $C(O)R^2$, $OR^2$, $OS(O)_2R^2$, $NR^2R^3$, $SR^2$, aryl and heteroaryl; and wherein $R^2$ and $R^3$ are defined as above;

D is a donor atom selected from N, O, S, P, Se and Te; and $R^{10}$ is selected from hydrogen or halo.

In one embodiment, $R^{10}$ is halo, for example bromine.

It will be appreciated that the embodiments described herein for $R^1$, Q, $Q^1$, $Q^2$, $Q^3$, $Q^4$, $Q^5$, $Q^6$, T, A, $A^1$ and D, in relation to compounds of Formula 1 or 2, can also provide embodiments for compounds of Formula 3 or 4, respectively.

In another aspect, there is provided a metal complex of Formula 5 or Formula 6:

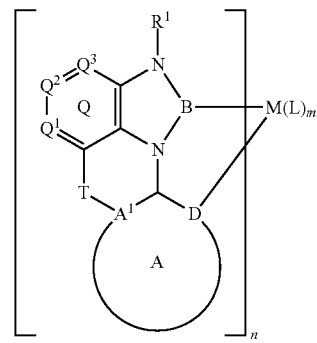

Formula 5

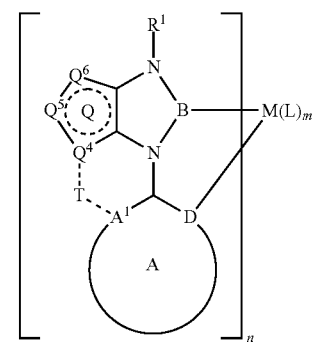

Formula 6 wherein

M is a metal atom selected from Ir, Pt, Rh, Pd, Ru and Os;

n is an integer selected from 1, 2 and 3;

m is an integer selected from 0, 1, 2, 3, 4, and 5;

L is a monodentate or bidentate ligand; and $R^1$ is selected from $C_{1-20}$alkyl, $C_{2-20}$alkenyl, $C_{2-20}$alkynyl, and a 5 or 6 membered aryl or heteroaryl, each of which is optionally substituted with one or more substituents independently selected from halo, CN, $NO_2$, $C(O)R^2$, $OR^2$, $OS(O)_2R^2$, $NR^2R^3$, $SR^2$, aryl and heteroaryl; wherein $R^2$ and $R^3$ are each independently selected from hydrogen and $C_{1-6}$alkyl;

Q is an optionally substituted, optionally fused 5 or 6 membered heterocyclic ring, wherein the dashed circle indicates the optional location of up to two optional double bonds in the ring; and $Q^1$, $Q^2$ and $Q^3$, are each independently selected from $CR^4$ or N; wherein at least one of $Q^1$, $Q^2$ and $Q^3$ is N; and $R^4$ is independently selected from hydrogen, halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, optionally substituted 5 or 6 membered aryl or heteroaryl, and optionally two $R^4$ substituents from adjacent ring atoms are joined together to form an optionally substituted 5 or 6 membered aryl or heteroaryl ring; wherein $R^2$ and $R^3$ are defined as above;

$Q^4$, $Q^5$ and $Q^6$, are each independently selected from N, S, O, $CR^4$ and $NR^5$, wherein at least one of $Q^4$, $Q^5$ and $Q^6$ is selected from N, S, O and $NR^5$; wherein $R^4$ is defined as above and $R^5$ is defined according to $R^1$ above; with the proviso that when T is present then $Q^4$ is selected from C-T and N-T, and when T is absent Q is not a furo[2,3-C]pyridine group;

T is a tether group between rings Q and A of 1 to 3 atoms in length linked together in a linear chain, wherein the dashed lines between $Q^4$ atom and A ring indicates T is an optional group, and wherein T is selected from C, N, O, S, Si and B, each of which is optionally substituted with one or more substituents independently selected from hydrogen, halo, CN, $NO_2$, =O, $C(O)R^2$, $OR^2$, $OS(O)_2R^2$, $NR^2R^3$, $SR^2$, optionally substituted $C_{1-10}$alkyl, optionally substituted $C_{2-10}$alkenyl, optionally substituted $C_{2-10}$alkynyl and optionally substituted 5 or 6 membered aryl or heteroaryl, and optionally fused with a 3-6 membered carbocycle or heterocycle; and wherein $R^2$ and $R^3$ are each independently defined as above, A is a monocyclic or bicyclic 5 or 6 membered heterocyclic ring containing a donor atom D and a ring atom $A^1$, and optionally having 1 or 2 additional ring heteroatoms selected from O, S and N, wherein the heterocyclic ring is optionally substituted with 1 to 3 substituents independently selected from halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, and optionally substituted 5 or 6 membered aryl or heteroaryl; wherein $R^2$ and $R^3$ are each independently defined as above;

$A^1$ is selected from C, O, S, N, $CR^8$, $C(R^8)_2$ and $NR^9$; wherein each $R^8$ is independently selected from hydrogen, halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, optionally substituted 5 or 6 membered aryl or heteroaryl; $R^9$ is selected from hydrogen, $C_{1-20}$alkyl, $C_{2-20}$alkenyl, $C_{2-20}$alkynyl, and a 5 or 6 membered aryl or heteroaryl, each of which can be optionally substituted with one or more substituents independently selected from halo, CN, $NO_2$, $C(O)R^2$, $OR^2$, $OS(O)_2R^2$, $NR^2R^3$, $SR^2$, aryl and heteroaryl; and wherein $R^2$ and $R^3$ are defined as above;

D is a donor atom selected from N, O, S, P, Se and Te.

It will be appreciated that the embodiments described herein for $R^1$, Q, $Q^1$, $Q^2$, $Q^3$, $Q^4$, $Q^5$, $Q^6$, T, A, $A^1$ and D, in relation to compounds of Formula 1 or 2, can also provide embodiments for compounds of Formula 5 or 6, respectively.

In one embodiment, M is a metal atom selected from Ir and Pt. In a particular embodiment, M is selected from Ir.

In one embodiment, n is 3, m is 0 and L is absent.

In another aspect, there is provided an emission material comprising a metal complex of Formula 5 or Formula 6, as described herein.

The emission material may comprise one or more matrix materials. The emission material may comprise one or more functional additives selected from hole-injection materials, hole-transport materials, hole-blocking materials, electron-transport materials, electron-injection materials, electron-blocking materials, exciton-blocking materials, charge-generation materials and/or organic or inorganic p/n junctions.

In another aspect, there is provided use of a metal complex of Formula 5 or Formula 6, as described herein, as an emission material in an electronic device. In one embodiment, the electronic device is an organic electroluminescent device.

In another aspect, there is provided a matrix material comprising a metal complex of Formula 5 or Formula 6 as described herein.

The matrix material may comprise one or more functional additives selected from emission materials, hole-injection materials, hole-transport materials, hole-blocking materials, electron-transport materials, electron-injection materials, electron-blocking materials, exciton-blocking materials, charge-generation materials and/or organic or inorganic p/n junctions.

In another aspect, there is provided use of a metal complex of Formula 5 or Formula 6, as described herein, as a matrix material in an electronic device. In one embodiment, the electronic device is an organic electroluminescent device.

In another aspect, there is provided an electronic device comprising a metal complex of Formula 5 or Formula 6 as described herein.

In another aspect, there is provided use of a metal complex of Formula 5 or Formula 6 as described herein, in an electronic device.

In one embodiment, the electronic device is an organic electroluminescent device. The organic electroluminescent device may be an organic light emitting device, a photovoltaic device or a sensor. The organic electroluminescent device may comprise: a pair of electrodes comprising a cathode and an anode; and at least one layer comprising an emission material arranged between the pair of electrodes comprising a metal complex of Formula 5 or Formula 6 as described herein. The organic electronic device may comprise further layers, selected from in each case one or more hole-injection layers, hole-transport layers, hole-blocking layers, electron-transport layers, electron-injection layers, electron-blocking layers, exciton-blocking layers, charge-generation layers and/or organic or inorganic p/n junctions.

In another aspect, there is provided a process for preparing a diamine compound according to Formula 1 or Formula 2 comprising the steps:

reacting an optionally substituted heterocyclic compound comprising a fused imidazole group with an optionally substituted monocyclic or bicyclic 5 or 6 membered heterocyclic ring comprising a donor atom D selected from N, O, S, P, Se and Te, to form an imidazyl N-substituted heterocyclic compound; and reacting the imidazyl N-substituted heterocyclic compound with a reducing agent to form a diamine compound of Formula 1 or Formula 2, as described herein.

In another aspect, there is provided a process for preparing a metal complex according to Formula 5 or Formula 6 comprising the steps:

reacting a diamine compound of Formula 1 or Formula 2
    with a boron agent to obtain a diazaborole compound of Formula 3 or Formula 4, respectively, as described herein;

reacting the diazaborole compound of Formula 3 or Formula 4 with a precursor complex of the metal M having substitutable ligands in a ratio suitable to obtain a product being a metal complex of Formula 5 or Formula 6 having the desired number n of diamine compounds of Formula 3 or Formula 4, and optionally ligands L, being co-ordinated to the metal M; and optionally further reacting the product with another ligand L in a ratio suitable to introduce the desired number of ligands L into the metal complex of Formula 5 or Formula 6.

Other features, objects and advantages of the present disclosure and its embodiments will become apparent from the detailed description, examples and claims that follow.

DETAILED DESCRIPTION

The present invention is described in the following various non-limiting embodiments, which relate to investigations undertaken to identify precursor compounds for preparing alternative or improved phosphorescent metal complexes. The metal complexes of the present disclosure can be used as an active component in electronic devices, such as an emission material in OLEDs.

General Terms

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Those skilled in the art will appreciate that the disclosure herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

Each example of the present disclosure described herein is to be applied mutatis mutandis to each and every other example unless specifically stated otherwise. The present disclosure is not to be limited in scope by the specific examples described herein, which are intended for the purpose of exemplification only. Functionally-equivalent products, compositions and methods are clearly within the scope of the disclosure as described herein.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be clearly understood that, although a number of prior art publications are referred to herein, this reference does not constitute an admission that any of these documents forms part of the common general knowledge in the art, in Australia or in any other country.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Specific Terms

The terms "carbocyclic" and "carbocyclyl" represent a ring system wherein the ring atoms are all carbon atoms, e.g., of about 3 to about 30 carbon atoms, and which may be aromatic, non-aromatic, saturated, or unsaturated, and may be substituted and/or carry fused rings. Examples of such groups include benzene, cyclopentyl, cyclohexyl, or fully or partially hydrogenated phenyl, naphthyl and fluorenyl.

"Heterocyclyl" or "heterocyclic" whether used alone, or in compound words such as heterocyclyloxy represents: (i) an optionally substituted cycloalkyl or cycloalkenyl group, e.g., of about 3 to about 30 ring members, which may contain one or more heteroatoms such as nitrogen, oxygen, or sulfur (examples include pyrrolidinyl, morpholino, thiomorpholino, or fully or partially hydrogenated thienyl, furyl, pyrrolyl, thiazolyl, oxazolyl, oxazinyl, thiazinyl, pyridyl and azepinyl); (ii) an optionally substituted partially saturated polycyclic ring system in which an aryl (or heteroaryl) ring and a heterocyclic group are fused together to form a cyclic structure (examples include chromanyl, dihydrobenzofuryl and indolinyl); or (iii) an optionally substituted fully or partially saturated polycyclic fused ring system that has one or more bridges (examples include quinuclidinyl and dihydro-1,4-epoxynaphthyl).

As will be understood, an "aromatic" group means a cyclic group having $4m+2\pi$ electrons, where m is an integer equal to or greater than 1. As used herein, "aromatic" is used interchangeably with "aryl" to refer to an aromatic group, regardless of the valency of aromatic group.

"Aryl" whether used alone, or in compound words such as arylalkyl, aryloxy or arylthio, represents: (i) an optionally substituted mono- or polycyclic aromatic carbocyclic moiety, e.g., of about 6 to about 30 carbon atoms, such as phenyl, naphthyl or fluorenyl; or, (ii) an optionally substituted partially saturated polycyclic carbocyclic aromatic ring system in which an aryl and a cycloalkyl or cycloalkenyl group are fused together to form a cyclic structure such as a tetrahydronaphthyl, indenyl, indanyl or fluorene ring.

A heteroaromatic group is an aromatic group or ring containing one or more heteroatoms, such as N, O, S, Se, Si or P. As used herein, "heteroaromatic" is used interchangeably with "heteroaryl", and a heteroaryl group refers to monovalent aromatic groups, bivalent aromatic groups and higher multivalency aromatic groups containing one or more heteroatoms.

"Heteroaryl" whether used alone, or in compound words such as heteroaryloxy represents: (i) an optionally substituted mono- or polycyclic aromatic organic moiety, e.g., of about 5 to about 30 ring members in which one or more of the ring members is/are element(s) other than carbon, for example nitrogen, oxygen, sulfur or silicon; the heteroatom(s) interrupting a carbocyclic ring structure and having a sufficient number of delocalized $\pi$ electrons to provide aromatic character, provided that the rings do not contain adjacent oxygen and/or sulfur atoms. Typical 6-membered heteroaryl groups are pyrazinyl, pyridazinyl, pyrazolyl, pyridyl and pyrimidinyl. All regioisomers are contemplated, e.g., 2-pyridyl, 3-pyridyl and 4-pyridyl. Typical 5-membered heteroaryl rings are furyl, imidazolyl, oxazolyl, isoxazolyl, isothiazolyl, oxadiazolyl, pyrrolyl, 1,3,4-thiadiazolyl, thiazolyl, thienyl, triazolyl, and silole. All regioisomers are contemplated, e.g., 2-thienyl and 3-thienyl. Bicyclic groups typically are benzo-fused ring systems derived from the heteroaryl groups named above, e.g., benzofuryl, benzimidazolyl, benzthiazolyl, indolyl, indolizinyl, isoquinolyl, quinazolinyl, quinolyl and benzothienyl; or, (ii) an optionally substituted partially saturated polycyclic heteroaryl ring system in which a heteroaryl and a cycloalkyl or cycloalkenyl group are fused together to form a cyclic structure such as a tetrahydroquinolyl or pyrindinyl ring.

The term "optionally fused" means that a group is either fused by another ring system or unfused, and "fused" refers to one or more rings that share at least two common ring atoms with one or more other rings. Fusing may be provided by one or more carbocyclic, heterocyclic, aryl or heteroaryl rings, as defined herein, or be provided by substituents of rings being joined together to form a further ring system. The fused ring may be a 5, 6 or 7 membered ring of between 5 and 10 ring atoms in size. The fused ring may be fused to one or more other rings, and may for example contain 1 to 4 rings.

The term "optionally substituted" means that a group is either substituted or unsubstituted, at any available position. Substitution can be with one or more groups selected from, e.g., alkyl, alkenyl, alkynyl, cycloalkyl, cycloalkenyl, aryl, heterocyclyl, heteroaryl, formyl, alkanoyl, cycloalkanoyl, aroyl, heteroaroyl, carboxyl, alkoxycarbonyl, cycloalkyloxycarbonyl, aryloxycarbonyl, heterocyclyloxycarbonyl, heteroaryloxycarbonyl, alkylaminocarbonyl, cycloalkylaminocarbonyl, arylaminocarbonyl, heterocyclylaminocarbonyl, heteroarylaminocarbonyl, cyano, alkoxy, cycloalkoxy, aryloxy, heterocyclyloxy, heteroaryloxy, alkanoate, cycloalkanoate, aryloate, heterocyclyloate, heteroaryloate, alkylcarbonylamino, cycloalkylcarbonylamino, arylcarbonylamino, heterocyclylcarbonylamino, heteroarylcarbonylamino, nitro, alkylthio, cycloalkylthio, arylthio, heterocyclylthio, heteroarylthio, alkylsulfonyl, cycloalkylsulfonyl, arylsulfonyl, heterocyclylsulfonyl, heteroarylsulfonyl, hydroxyl, halo, haloalkyl, haloaryl, haloheterocyclyl, haloheteroaryl, haloalkoxy, haloalkylsulfonyl, silylalkyl, alkenylsilylalkyl, and alkynylsilylalkyl. It will be appreciated that other groups not specifically described may also be used.

In addition to the disclosure herein, in a certain embodiment, a group that is substituted has 1, 2, 3, or 4 substituents, 1, 2, or 3 substituents, 1 or 2 substituents, or 1 substituent.

The term "halo" or "halogen" whether employed alone or in compound words such as haloalkyl, haloalkoxy or haloalkylsulfonyl, represents fluorine, chlorine, bromine or iodine. Further, when used in compound words such as haloalkyl, haloalkoxy or haloalkylsulfonyl, the alkyl may be partially halogenated or fully substituted with halogen atoms which may be independently the same or different. Examples of haloalkyl include, without limitation, —CH$_2$CH$_2$F, —CF$_2$CF$_3$ and —CH$_2$CHFCl. Examples of haloalkoxy include, without limitation, —OCHF$_2$, —OCF$_3$, —OCH$_2$CCl$_3$, —OCH$_2$CF$_3$ and —OCH$_2$CH$_2$CF$_3$. Examples of haloalkylsulfonyl include, without limitation, —SO$_2$CF$_3$, —SO$_2$CCl$_3$, —SO$_2$CH$_2$CF$_3$ and —SO$_2$CF$_2$CF$_3$.

"Alkyl" whether used alone, or in compound words such as alkoxy, alkylthio, alkylamino, dialkylamino or haloalkyl, represents straight or branched chain hydrocarbons ranging in size from one to about 20 carbon atoms, or more. Thus alkyl moieties include, unless explicitly limited to smaller groups, moieties ranging in size, for example, from one to about 6 carbon atoms or greater, such as, methyl, ethyl, n-propyl, iso-propyl and/or butyl, pentyl, hexyl, and higher isomers, including, e.g., those straight or branched chain hydrocarbons ranging in size from about 6 to about 20 carbon atoms, or greater.

"Alkenyl" whether used alone, or in compound words such as alkenyloxy or haloalkenyl, represents straight or branched chain hydrocarbons containing at least one carbon-carbon double bond, including, unless explicitly limited to smaller groups, moieties ranging in size from two to about 6 carbon atoms or greater, such as, methylene, ethylene, 1-propenyl, 2-propenyl, and/or butenyl, pentenyl, hexenyl, and higher isomers, including, e.g., those straight or branched chain hydrocarbons ranging in size, for example, from about 6 to about 20 carbon atoms, or greater.

"Alkynyl" whether used alone, or in compound words such as alkynyloxy, represents straight or branched chain hydrocarbons containing at least one carbon-carbon triple bond, including, unless explicitly limited to smaller groups, moieties ranging in size from, e.g., two to about 6 carbon atoms or greater, such as, ethynyl, 1-propynyl, 2-propynyl, and/or butynyl, pentynyl, hexynyl, and higher isomers, including, e.g., those straight or branched chain hydrocarbons ranging in size from, e.g., about 6 to about 20 carbon atoms, or greater.

"Cycloalkyl" represents a mono- or polycarbocyclic ring system of varying sizes, e.g., from about 3 to about 20 carbon atoms, e.g., cyclopropyl, cyclobutyl, cyclopentyl, cyclohexyl or cycloheptyl. The term cycloalkyloxy represents the same groups linked through an oxygen atom such as cyclopentyloxy and cyclohexyloxy. The term cycloalkylthio represents the same groups linked through a sulfur atom such as cyclopentylthio and cyclohexylthio.

"Cycloalkenyl" represents a non-aromatic mono- or polycarbocyclic ring system, e.g., of about 3 to about 20 carbon atoms containing at least one carbon-carbon double bond, e.g., cyclopentenyl, cyclohexenyl or cycloheptenyl. The term "cycloalkenyloxy" represents the same groups linked through an oxygen atom such as cyclopentenyloxy and cyclohexenyloxy. The term "cycloalkenylthio" represents the same groups linked through a sulfur atom such as cyclopentenylthio and cyclohexenylthio.

"Cycloalkynyl" represents a non-aromatic mono- or polycarbocyclic ring system, e.g., of about 3 to about 20 carbon atoms containing at least one carbon-carbon double bond, e.g., cyclopentenyl, cyclohexenyl or cycloheptenyl. The term "cycloalkenyloxy" represents the same groups linked through an oxygen atom such as cyclopentenyloxy and cyclohexenyloxy. The term "cycloalkenylthio" represents the same groups linked through a sulfur atom such as cyclopentenylthio and cyclohexenylthio.

"Formyl" represents a —CHO moiety.

"Alkanoyl" represents a —C(=O)-alkyl group in which the alkyl group is as defined supra. In a particular embodiment, an alkanoyl ranges in size from about $C_2$-$C_{20}$. One example is acyl.

"Aroyl" represents a —C(=O)-aryl group in which the aryl group is as defined supra. In a particular embodiment, an aroyl ranges in size from about $C_7$-$C_{20}$. Examples include benzoyl and 1-naphthoyl and 2-naphthoyl.

"Heterocycloyl" represents a —C(=O)-heterocyclyl group in which the heterocyclic group is as defined supra. In a particular embodiment, an heterocyclyl ranges in size from about $C_4$-$C_{20}$.

"Heteroaroyl" represents a —C(=O)-heteroaryl group in which the heteroaryl group is as defined supra. In a particular embodiment, a heteroaroyl ranges in size from about $C_6$-$C_{20}$. An example is pyridylcarbonyl.

"Carboxyl" represents a —CO$_2$H moiety.

"Oxycarbonyl" represents a carboxylic acid ester group —CO$_2$R which is linked to the rest of the molecule through a carbon atom.

"Alkoxycarbonyl" represents an —CO$_2$-alkyl group in which the alkyl group is as defined supra. In a particular embodiment, an alkoxycarbonyl ranges in size from about $C_2$-$C_{20}$. Examples include methoxycarbonyl and ethoxycarbonyl.

"Aryloxycarbonyl" represents an —CO$_2$-aryl group in which the aryl group is as defined supra. Examples include phenoxycarbonyl and naphthoxycarbonyl.

"Heterocyclyloxycarbonyl" represents a —CO₂-heterocyclyl group in which the heterocyclic group is as defined supra.

"Heteroaryloxycarbonyl" represents a —CO-heteroaryl group in which the heteroaryl group is as defined supra.

"Aminocarbonyl" represents a carboxylic acid amide group —C(=O)NHR or —C(=O)NR₂ which is linked to the rest of the molecule through a carbon atom.

"Alkylaminocarbonyl" represents a —C(=O)NHR or —C(=O)NR₂ group in which R is an alkyl group as defined supra.

"Arylaminocarbonyl" represents a —C(=O)NHR or —C(=O)NR₂ group in which R is an aryl group as defined supra.

"Heterocyclylaminocarbonyl" represents a —C(=O)NHR or —C(=O)NR₂ group in which R is a heterocyclic group as defined supra. In certain embodiments, NR₂ is a heterocyclic ring, which is optionally substituted.

"Heteroarylaminocarbonyl" represents a —C(=O)NHR or —C(=O)NR₂ group in which R is a heteroaryl group as defined supra. In certain embodiments, NR₂ is a heteroaryl ring, which is optionally substituted.

"Cyano" represents a —CN moiety.

"Hydroxyl" represents a —OH moiety.

"Alkoxy" represents an —O-alkyl group in which the alkyl group is as defined supra. Examples include methoxy, ethoxy, n-propoxy, iso-propoxy, and the different butoxy, pentoxy, hexyloxy and higher isomers.

"Aryloxy" represents an —O-aryl group in which the aryl group is as defined supra. Examples include, without limitation, phenoxy and naphthoxy.

"Alkenyloxy" represents an —O-alkenyl group in which the alkenyl group is as defined supra. An example is allyloxy.

"Heterocyclyloxy" represents an —O-heterocyclyl group in which the heterocyclic group is as defined supra.

"Heteroaryloxy" represents an —O-heteroaryl group in which the heteroaryl group is as defined supra. An example is pyridyloxy.

"Alkanoate" represents an —OC(=O)—R group in which R is an alkyl group as defined supra.

"Aryloate" represents a —OC(=O)—R group in which R is an aryl group as defined supra.

"Heterocyclyloate" represents an —OC(=O)—R group in which R is a heterocyclic group as defined supra.

"Heteroaryloate" represents an —OC(=O)—R group in which P is a heteroaryl group as defined supra.

"Amino" represents an —NH₂ moiety.

"Alkylamino" represents an —NHR or —NR₂ group in which R is an alkyl group as defined supra. Examples include, without limitation, methylamino, ethylamino, n-propylamino, isopropylamino, and the different butylamino, pentylamino, hexylamino and higher isomers.

"Arylamino" represents an —NHR or —NR₂ group in which R is an aryl group as defined supra. An example is phenylamino.

"Heterocyclylamino" represents an —NHR or —NR₂ group in which R is a heterocyclic group as defined supra. In certain embodiments, NR₂ is a heterocyclic ring, which is optionally substituted.

"Heteroarylamino" represents a —NHR or —NR₂ group in which R is a heteroaryl group as defined supra. In certain embodiments, NR₂ is a heteroaryl ring, which is optionally substituted.

"Carbonylamino" represents a carboxylic acid amide group —NHC(=O)R that is linked to the rest of the molecule through a nitrogen atom.

"Alkylcarbonylamino" represents a —NHC(=O)R group in which R is an alkyl group as defined supra.

"Arylcarbonylamino" represents an —NHC(=O)R group in which R is an aryl group as defined supra.

"Heterocyclylcarbonylamino" represents an —NHC(=O)R group in which R is a heterocyclic group as defined supra.

"Heteroarylcarbonylamino" represents an —NHC(=O)R group in which R is a heteroaryl group as defined supra.

"Nitro" represents a —NO₂ moiety.

"Alkylthio" represents an —S-alkyl group in which the alkyl group is as defined supra. Examples include, without limitation, methylthio, ethylthio, n-propylthio, iso propylthio, and the different butylthio, pentylthio, hexylthio and higher isomers.

"Arylthio" represents an —S-aryl group in which the aryl group is as defined supra. Examples include phenylthio and naphthylthio.

"Heterocyclylthio" represents an —S-heterocyclyl group in which the heterocyclic group is as defined supra.

"Heteroarylthio" represents an —S-heteroaryl group in which the heteroaryl group is as defined supra.

"Sulfonyl" represents an —SO₂R group that is linked to the rest of the molecule through a sulfur atom.

"Alkylsulfonyl" represents an —SO₂-alkyl group in which the alkyl group is as defined supra.

"Arylsulfonyl" represents an —SO₂-aryl group in which the aryl group is as defined supra.

"Heterocyclylsulfonyl" represents an —SO₂-heterocyclyl group in which the heterocyclic group is as defined supra.

"Heteoarylsulfonyl" presents an —SO₂-heteroaryl group in which the heteroaryl group is as defined supra.

"Aldehyde" represents a —C(=O)H group.

"Alkanal" represents an alkyl-(C=O)H group in which the alkyl group is as defined supra.

"Alkylsilyl" presents an alkyl group that is linked to the rest of the molecule through the silicon atom, which may be substituted with up to three independently selected alkyl groups in which each alkyl group is as defined supra.

"Alkenylsilyl" presents an alkenyl group that is linked to the rest of the molecule through the silicon atom, which may be substituted with up to three independently selected alkenyl groups in which each alkenyl group is as defined supra.

"Alkynylsilyl" presents an alkynyl group that is linked to the rest of the molecule through the silicon atom, which may be substituted with up to three independently selected alkynyl groups in which each alkenyl group is as defined supra.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR⁷⁰, =N—OR⁷⁰, =N₂ or =S) on saturated carbon atoms in the specified group or radical are, unless otherwise specified, —R⁶⁰, halo, =O, —OR⁷⁰, —SR⁷⁰, —NR⁸⁰R⁸⁰, trihalomethyl, —CN, —OCN, —SCN, —NO, —NO₂, =N₂, —N₃, —SO₂R⁷⁰, —SO₂O⁻M⁺, —SO₂OR⁷⁰, —OSO₂R⁷⁰, —OSO₂O⁻M⁺, —OSO₂OR⁷⁰, —P(O)(O⁻)₂(M⁺)₂, —P(O)(OR⁷⁰)O⁻M⁺, —P(O)(OR⁷)₂, —C(O)R⁷⁰, —C(S)R⁷⁰, —C(NR⁷⁰)R⁷⁰, —C(O)O⁻M⁺, —C(O)OR⁷⁰, —C(S)OR⁷⁰, —C(O)NR⁸⁰R⁸⁰, —C(NR⁷⁰)NR⁸⁰R⁸⁰, —OC(O)R⁷⁰, —OC(S)R⁷⁰, —OC(O)O⁻M⁺, —OC(O)OR⁷⁰, —OC(S)OR⁷⁰, —NR⁷⁰C (O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as +N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the present disclosure and the other a typical counter ion such as chloride, or two ionized compounds disclosed herein can serve as counter ions for such divalent alkali earth ions, or a doubly ionized compound of the present disclosure can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

Diamine Compounds

The present disclosure provides diamine compounds of Formula 1 or Formula 2 as described below. The diamine compounds can be used as precursors in preparing phosphorescent diazaborole metal complexes, which are suitable for use as emission materials or within emission materials and electronic devices, such as OLEDs. Each diamine compound contains two secondary amine groups attached in an ortho arrangement to a 5 or 6 membered heterocyclic group (i.e. 1,2-attachment at adjacent ring atoms). The two secondary amine groups can provide a chelating group for a phosphorescent boron metal complex. In the diamine compounds, one of the secondary amine groups is also attached to a further 5 or 6 membered heterocyclic group containing a donor atom D for coordination to a metal atom.

The diamine compounds of Formula 1 or Formula 2 are described in further detail below, and generally by the following structures:

Formula 1

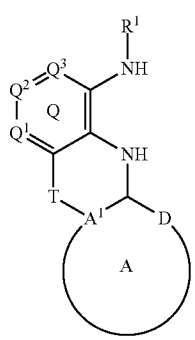

Formula 2

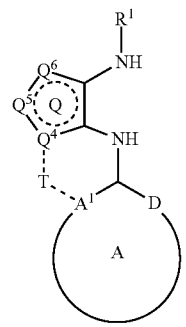

wherein R$^1$, Q, Q$^1$, Q$^2$, Q$^3$ Q$^4$, Q$^5$, Q$^6$, T, A, A$^1$ and D, can be defined as described herein.

R$^1$ Group

In some embodiments, R$^1$ can be selected from C$_{1-20}$alkyl, C$_{2-20}$alkenyl, C$_{2-20}$alkynyl, and a 5 or 6 membered aryl or heteroaryl, each of which can be optionally substituted with one or more substituents. The one or more substituents of the above described R$^1$ groups may be each independently selected from halo, CN, NO$_2$, C(O)R$^2$, OR$^2$, OS(O)$_2$R$^2$, NR$^2$R$^3$, SR$^2$, aryl and heteroaryl. R$^2$ and R$^3$ can each be independently selected from hydrogen and C$_{1-6}$alkyl. The 5 or 6 membered aryl or heteroaryl may be monocyclic such as benzene and pyridine, bicyclic such as naphthalene, phenylbenzene and quinoline, or tricyclic such as anthracene, diphenylbenzene and acridine. In one embodiment, R$^1$ is selected from optionally substituted C$_{1-20}$alkyl and optionally substituted monocyclic 5 or 6 membered aryl or heteroaryl. In another embodiment, R$^1$ is selected from optionally substituted C$_{1-10}$alkyl.

Ring Q

In some embodiments, Q is a 5 or 6-membered heterocyclic ring that may be optionally substituted and optionally fused with one or more substituents or groups. In one embodiment, Q is an optionally substituted, optionally fused 5 or 6-membered heteroaromatic ring.

The one or more optional substituents of the Q ring may be selected from halo, CN, NO$_2$, C(O)R$^2$, OR$^2$, OS(O)$_2$R$^2$, NR$^2$R$^3$, SR$^2$, optionally substituted C$_{1-20}$alkyl, optionally substituted C$_{2-20}$alkenyl, optionally substituted C$_{2-20}$alkynyl, and optionally substituted 5 or 6 membered aryl or heteroaryl. R$^2$ and R$^3$ can each be independently selected from hydrogen and C$_{1-6}$alkyl. In one embodiment, the optionally substituted 5 or 6 membered aryl or heteroaryl group is monocyclic such as benzene and pyridine or bicyclic such as naphthalene, phenylbenzene and quinoline.

The optionally fused groups to the Q ring may be selected from optionally substituted 5 or 6 membered aryl or heteroaryl. In one embodiment, the optionally substituted 5 or 6 membered aryl or heteroaryl group is monocyclic such as benzene and pyridine or bicyclic such as naphthalene, phenylbenzene and quinoline. In another embodiment, the optional fused group to the Q ring is an optionally substituted benzene, for example where the Q group is optionally substituted quinolone or benzothiophene.

6 Membered Heterocyclic Q Rings

In some embodiments, for compounds of Formula 1, Q is an optionally substituted, optionally fused, 6-membered heteroaromatic ring. Q$^1$, Q$^2$ and Q$^3$ can be each independently selected from CR$^4$ or N; wherein at least one of Q$^1$, Q$^2$ and Q$^3$ is N.

In some embodiments, $R^4$ can be independently selected from hydrogen, halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, and optionally substituted 5 or 6 membered aryl or heteroaryl. Optionally, two $R^4$ substituents from adjacent ring atoms can also be joined together to form an optionally substituted 5 or 6 membered aryl or heteroaryl ring fused to the B ring. $R^2$ and $R^3$ can be defined as described above.

The optionally substituted 5 or 6 membered aryl or heteroaryl group may be selected from a monocyclic group, such as optionally substituted benzene and pyridine, or a bicyclic group, such as optionally substituted naphthalene, phenylbenzene and quinoline.

Examples of 6-membered heterocyclic aromatic rings for Q, which may be optionally substituted or optionally fused by one or more additional groups, are N and C atom containing heterocyclic rings, such as pyridine, pyridazines, pyrimidines.

In some embodiments, Q is a pyridine ring. In some embodiments, Q is a pyridazine ring. In some embodiments, Q is a pyrimidine ring. In some embodiments, $Q^1$ is $CR^4$, $Q^2$ is N and $Q^3$ is N. In some embodiments, $Q^1$ is N, $Q^2$ is $CR^4$ and $Q^3$ is N. In some embodiments, $Q^1$ is $CR^4$, $Q^2$ is N and $Q^3$ is $CR^4$. In some embodiments, $Q^1$ is N, $Q^2$ is $CR^4$ and $Q^3$ is $CR^4$ where the adjacent $R^4$ groups are joined together to form an optionally substituted aryl or heteroaryl ring.

In certain embodiments, the adjacent $R^4$ groups are joined together to form an optionally substituted fused benzo ring.

In some embodiments, Q is not fused to an additional ring at positions $Q^1$-$Q^3$. In some embodiments, Q is not fused to an additional ring at positions $Q^5$-$Q^6$. In some embodiments of Formula 2, where T is absent, Q is not fused to an additional ring at positions $Q^4$-$Q^6$.

Specific examples of 6-membered heterocyclic groups Q according to compounds of Formula 1 are provided as follows:

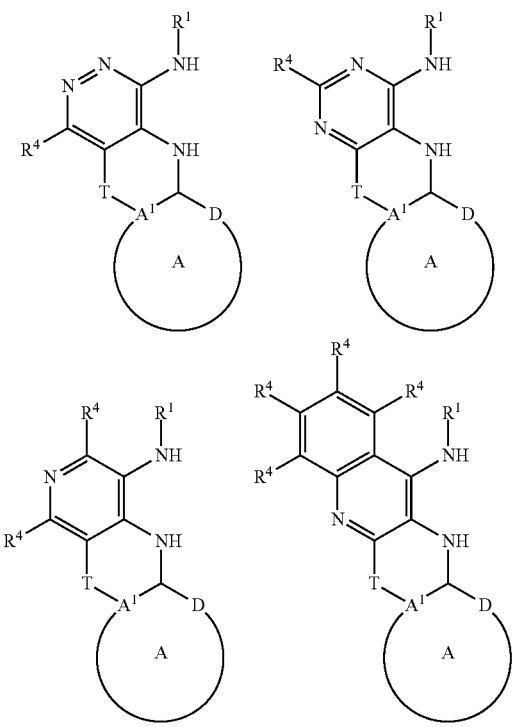

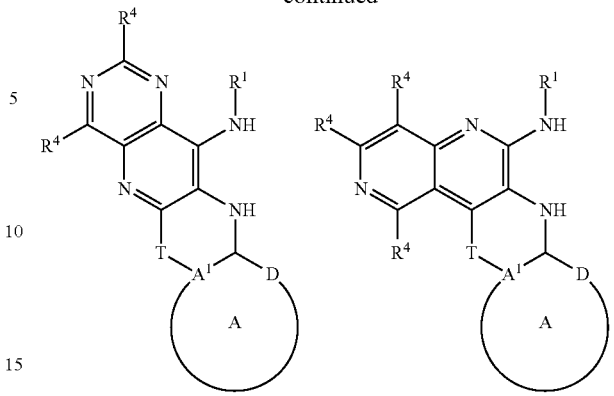

wherein A, $A^1$, D and $R^1$, can be defined as described herein, and each $R^4$ group can be independently selected from $R^4$ groups as described herein, including any embodiments thereof as described herein.

5 Membered Heterocyclic Q Rings

For compounds of Formula 2, Q is an optionally substituted, optionally fused, 5 membered heterocyclic ring. In one embodiment, Q is an optionally substituted, optionally fused 5-membered heteroaromatic ring. For compounds of Formula 2, the dashed circle in ring Q indicates the optional location of up to two optional double bonds in the ring. It will be appreciated that each double bond in the ring provides an additional π (pi) bond, for example Q may be an imidazole group.

Q may be a 5-membered aromatic or non-aromatic heterocyclic group having one or more heteroatoms. The heteroatoms may be selected from N, S and O.

$Q^4$, $Q^5$ and $Q^6$ can each be independently selected from N, S, O, $CR^4$ and $NR^5$, wherein at least one of $Q^4$, $Q^5$ and $Q^6$ is selected from N, S, O and $NR^5$. Each $R^4$ can be independently selected from $R^4$ groups as described herein. Each $R^5$ can be independently selected from hydrogen, optionally substituted $C_{1-20}$alkyl, optionally substituted $C_{2-20}$alkenyl, optionally substituted $C_{2-20}$alkynyl, and optionally substituted 5 or 6 membered aryl or heteroaryl. The optional substitution may be with one or more substituents independently selected from halo, CN, $NO_2$, $C(O)R^2$, $OR^2$, $OS(O)_2R^2$, $NR^2R^3$, $SR^2$, aryl and heteroaryl. $R^2$ and $R^3$ can each be independently selected from hydrogen and $C_{1-6}$alkyl.

It will be appreciated that since the tether group T is optional for compounds of Formula 2, then when T is present $Q^4$ is selected from C-T and N-T.

In another embodiment, when T is absent Q is not a furopyridine group, for example $Q^4$, $Q^5$ and $Q^6$, are each independently selected from N, S, $CR^4$ and $NR^5$, wherein at least one of $Q^4$, $Q^5$ and $Q^6$ is selected from N, S and $NR^5$. In another embodiment, $Q^4$, $Q^5$ and $Q^6$, are each independently selected from N, S and $CR^4$, wherein at least one of $Q^4$, $Q^5$ and $Q^6$ is selected from N and S. In a particular embodiment, $Q^5$ is S and $Q^4$ and $Q^5$ are $CR^4$.

In one embodiment, the compound of Formula 2 may be selected from a compound of Formula 2a or 2b:

Formula 2a

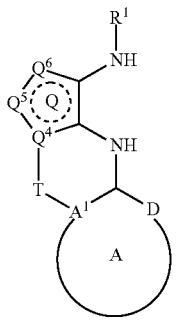

Formula 2b

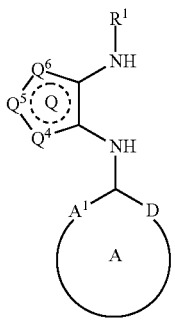

wherein $R^1$, Q, $Q^4$, $Q^5$, $Q^6$, T, A, $A^1$, and D, can be defined as described herein.

Examples of 5 membered heterocyclic rings for Q, which may be optionally substituted or optionally fused with one or more additional groups, are as follows: N and C atom containing heterocyclic rings, such as pyrazoles, pyrazolines, imidazoles, imidazolines, triazoles; S and C atom containing heterocyclic rings, such as thiophene; O and C atom containing heterocyclic rings, such as furan; N, C and O atom containing rings, such as oxazoles oxazolines, oxadiazoles; N, C and S atom containing rings, such as thiazoles, thiazolines.

In some embodiments, $Q^4$ is C-T, $Q^5$ is S and $Q^6$ is $CR^4$. In some embodiments, $Q^4$ is N-T, $Q^5$ is N and $Q^6$ is $CR^4$. In some embodiments, $Q^4$ is C-T, $Q^5$ is O and $Q^6$ is $CR^4$. In some embodiments, $Q^4$ is C-T, $Q^5$ is $NR^5$ and $Q^6$ is $CR^4$. In some embodiments, $Q^4$ is C-T, $Q^5$ is O and $Q^6$ is N. In some embodiments, $Q^4$ is C-T, $Q^5$ is $NR^5$ and $Q^6$ is N. In some embodiments of Formula 2, T is present.

Specific examples of 5-membered heterocyclic groups Q according to compounds of Formula 2a are provided as follows:

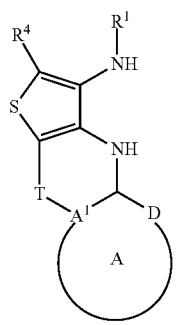 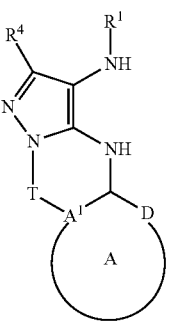 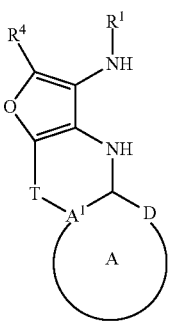

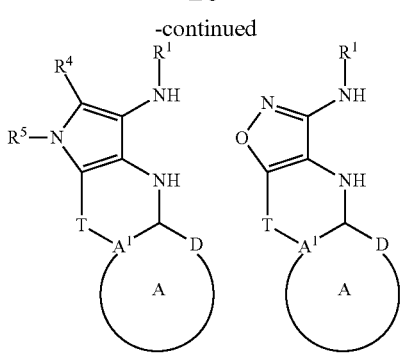

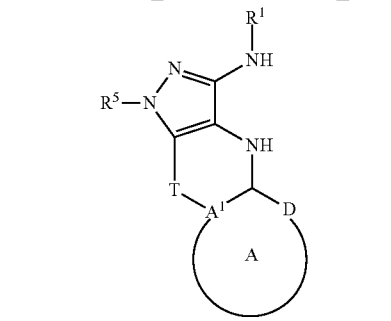

wherein A, $A^1$, D, T and $R^1$ can be defined as described herein, each $R^4$ can be independently selected from $R^4$ groups described herein, and each $R^5$ group can be independently selected from $R^5$ groups as described herein, including any embodiments thereof as described herein.

In some embodiments, $Q^4$ is $CR^4$, $Q^5$ is S and $Q^6$ is $CR^4$. In some embodiments, $Q^4$ is S, $Q^5$ is $CR^4$ and $Q^6$ is $CR^4$. In some embodiments, $Q^4$ is $CR^4$, $Q^5$ is O and $Q^6$ is $CR^4$. In some embodiments, $Q^4$ is $CR^4$, $Q^5$ is $NR^5$ and $Q^6$ is $CR^4$. In some embodiments, $Q^4$ is $CR^4$, $Q^5$ is O and $Q^6$ is N. In some embodiments, $Q^4$ is $CR^4$, $Q^5$ is $NR^5$ and $Q^6$ is N. In some embodiments, $Q^4$ is N, $Q^5$ is $NR^5$ and $Q^6$ is $CR^4$. In some embodiments, $Q^4$ is $NR^5$, $Q^5$ is N and $Q^6$ is $CR^4$. In some embodiments, $Q^4$ is $NR^5$, $Q^5$ is $CR^4$ and $Q^6$ is N. In some embodiments, $Q^4$ is S, $Q^5$ is $CR^4$ and $Q^6$ is N. In some embodiments, $Q^4$ is O, $Q^5$ is $CR^4$ and $Q^6$ is N. In some embodiments, $Q^4$ is S, $Q^5$ is $CR^4$ and $Q^6$ is $CR^4$, where the adjacent $R^4$ groups are joined together to form an optionally substituted aryl or heteroaryl ring. In certain embodiments, the adjacent $R^4$ groups are joined together to form an optionally substituted fused benzo ring.

In some embodiments, $Q^4$ is $CR^4$, $Q^5$ is $NR^4$ and $Q^6$ is $CR^4$, where two of the adjacent $R^4$ groups are joined together to form an optionally substituted aryl or heteroaryl ring. In certain embodiments, the $R^4$ groups located at the adjacent $Q^4$ and $Q^5$ positions are joined together to form an optionally substituted fused six membered heteroaryl ring (e.g., a fused ring including 1 or 2 N atoms in total).

In some embodiments, $Q^4$ is $NR^4$, $Q^5$ is $CR^4$ and $Q^6$ is N, where the adjacent $R^4$ groups are joined together to form an optionally substituted aryl or heteroaryl ring. In certain embodiments, the $R^4$ groups located at the adjacent $Q^4$ and $Q^5$ positions are joined together to form an optionally substituted fused six membered heteroaryl ring (e.g., a fused ring including 1 or 2 N atoms in total).

In some embodiments, $Q^4$ is $CR^4$, $Q^5$ is $NR^4$ and $Q^6$ is N, where the adjacent $R^4$ groups are joined together to form an optionally substituted aryl or heteroaryl ring. In certain embodiments, the adjacent $R^4$ groups are joined together to form an optionally substituted fused six membered heteroaryl ring (e.g., a fused ring including 1 or 2 N atoms in total).

Specific examples of 5-membered heterocyclic groups Q according to compounds of Formula 2b, when the tether group T is absent, are provided as follows:

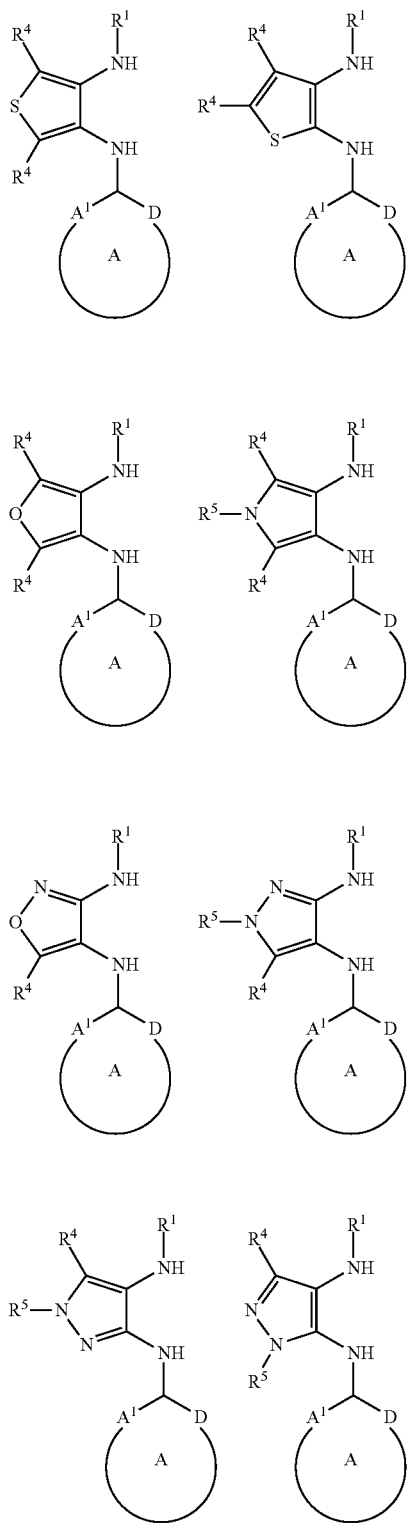

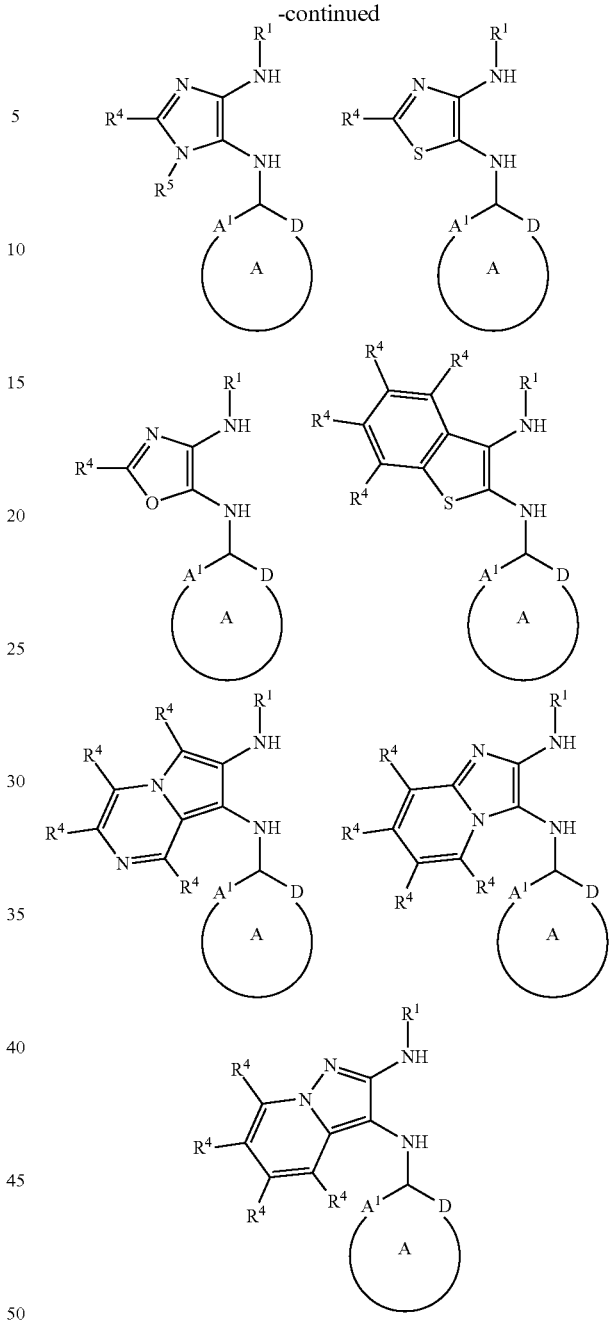

wherein A, A$^1$, D and R$^1$ can be defined as described herein, each R$^4$ can be independently selected from R$^4$ groups as described herein, and each R$^5$ group can be independently selected from R$^5$ groups as described herein, including any embodiments thereof as described herein.

Tether Group T

T is a tether group between rings Q and A of 1 to 3 atoms in length linked together in a linear chain. For compounds of Formula 2, the dashed lines between Q$^4$ atom and A ring indicates T is an optional group.

In one embodiment, T is a tether group provided by a linear chain of 1 to 3 atoms in length independently selected from C, N, O, S, Si and B. In another embodiment, the atoms are independently selected from C, N, O and S. Each of the 1 to 3 atoms can be optionally substituted. The optional substitution may be with one or more substituents independently selected from hydrogen, halo, CN, NO$_2$, =O, C(O)R$^2$, OR$^2$, OS(O)$_2$R$^2$, NR$^2$R$^3$, SR$^2$, optionally substituted C$_{1-10}$alkyl, optionally substituted C$_{2-10}$alkenyl, optionally substituted C$_{2-10}$alkynyl and optionally substituted 5 or 6 membered aryl or heteroaryl. R$^2$ and R$^3$ can each be independently defined as herein described. T may be optionally fused with a 3-6 membered carbocycle or heterocycle, for example where T is provided by a linear chain of 2 or 3 atoms then a 3-6 membered ring may be fused to 2 atoms of the linear chain. The optionally fused 3-6 membered carbocycle or heterocycle can be selected from an optionally substituted C$_{3-6}$cycloalkyl, optionally substituted phenyl, optionally substituted 5 or 6 membered heterocycle, or optionally substituted 5 or 6 membered heteroaryl.

In another embodiment, T can be a tether group provided by a linear chain of 1 to 3 atoms in length independently selected from —N(R$^7$)—, —N(R$^7$)—C(=O)—, —O—, —O—C(=O)—, —C(=O)—, —S—, —S(=O)—, —S(=O)$_2$—, —Si(R$^6$)$_2$—, —B(R$^7$)—, C$_{1-3}$alkyl and C$_{2-3}$alkenyl, each of which may be optionally substituted and optionally fused. In another embodiment, T can be a tether group provided by a linear chain of 1 to 3 atoms in length independently selected from —N(R$^7$)—, —N(R$^7$)—C(=O)—, —O—, —O—C(=O)—, —C(=O)—, —S—, —S(=O)—, —S(=O)$_2$—, C$_{1-3}$alkyl and C$_{2-3}$alkenyl, each of which may be optionally substituted and optionally fused. The C$_{1-3}$alkyl or C$_{2-3}$alkenyl can be optionally interrupted by a group selected from —N(R$^7$)—, —N(R$^7$)—C(=O)—, —O—, —O—C(=O)—, —C(=O)—, —S—, —S(=O)— and S(=O)$_2$. The C$_{1-3}$alkyl or C$_{2-3}$alkenyl can be optionally substituted with one or more substituents independently selected from halo, CN, NO$_2$, C(O)R$^2$, OR$^2$, OS(O)$_2$R$^2$, NR$^2$R$^3$, SR$^2$, C$_{1-10}$alkyl, C$_{2-10}$alkenyl, C$_{2-10}$alkynyl, C$_{1-10}$alkylhalo, C$_{2-10}$alkenylhalo and C$_{2-10}$alkynylhalo. In one embodiment, the C$_{1-3}$alkyl or C$_{2-3}$alkenyl is substituted with one or more optionally substituted C$_{1-4}$alkyl groups, for example where T is —C(CH$_3$)$_2$—, —C(CH$_3$)=C(CH$_3$)— or —C(CH$_2$Cl)$_2$—C(CH$_3$)$_2$—. R$^2$ and R$^3$ can each be independently defined as described above, including embodiments thereof. Each R$^7$ can be independently selected from R$^5$ as described herein, including embodiments thereof. The C$_{1-3}$alkyl or C$_{2-3}$alkenyl can be optionally fused with a 3-6 membered carbocycle or heterocycle, such as an optionally substituted C$_{3-6}$cycloalkyl, optionally substituted phenyl, optionally substituted 5 or 6 membered heterocycle, or optionally substituted 5 or 6 membered heteroaryl.

In another embodiment, T is an optionally substituted, optionally fused C$_{1-3}$ group, for example an optionally substituted, optionally fused C$_{1-3}$alkyl or C$_{2-3}$alkenyl. The C$_{1-3}$alkyl or C$_{2-3}$alkenyl can be optionally interrupted by a group selected from —N(R$^6$)—, —N(R$^6$)—C(=O)—, —O—, —O—C(=O)—, —C(=O)—, —S—, —S(=O)— and S(=O)$_2$. The optional substituents and optional fusing may be provided as described above.

In another embodiment, the optional substitution on the tether group T may be independently selected from optionally substituted C$_{1-10}$alkyl, for example optionally substituted methyl, ethyl or propyl.

Specific examples of the tether group T for compounds of Formula 1 are provided as follows:

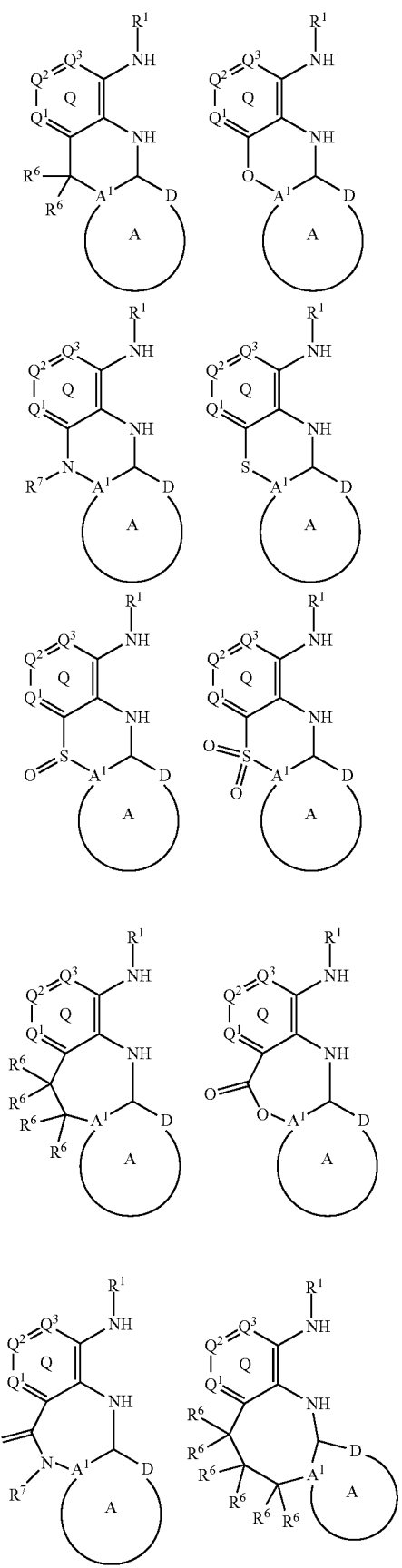

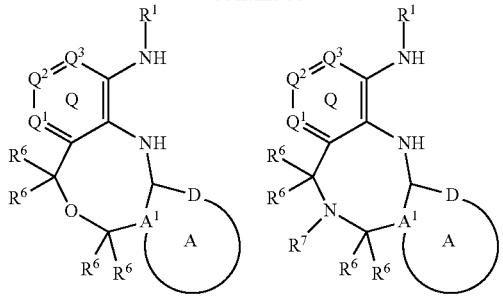

wherein Q, $Q^1$, $Q^2$, $Q^3$, A, $A^1$, D and $R^1$, can be defined as described herein, each $R^6$ group can be independently selected from $R^4$ groups described herein, and each $R^7$ group can be independently selected from $R^5$ groups as described herein, including any embodiments thereof as described herein.

In one embodiment, each $R^7$ can be selected from hydrogen and $C_{1-10}$alkyl. In another embodiment, $R^6$ is optionally substituted with one or more substituents independently selected from halo, CN, $NO_2$, $C(O)R^2$, $OR^2$, $OS(O)_2R^2$, $NR^2R^3$, $SR^2$, $C_{1-10}$alkyl, $C_{2-10}$alkenyl, $C_{2-10}$alkynyl, $C_{1-10}$alkylhalo, $C_{2-10}$alkenylhalo and $C_{2-10}$alkynylhalo. In a further embodiment, $R^6$ is substituted with one or more optionally substituted $C_{1-4}$alkyl groups, for example methyl or bromoethyl. $R^2$ and $R^3$ can be defined as described herein.

It will be appreciated that the above specific examples of the tether group T according to compounds of Formula 1 may also be provided as embodiments of the tether group T for compounds of Formula 2a.

Ring A

In some embodiments, A is a monocyclic or bicyclic 5 or 6 membered heterocyclic ring containing a donor atom D and a ring atom $A^1$. The A ring can optionally have 1 or 2 additional ring heteroatoms selected from O, S and N. In one embodiment, A is an optionally substituted monocyclic or bicyclic 5 or 6 membered heterocyclic ring containing at least one unsaturated bond. In another embodiment, A is an optionally substituted monocyclic or bicyclic 5 or 6 membered heteroaryl ring. In a particular embodiment, A is an optionally substituted monocyclic ring.

In some embodiments, the A ring can be optionally substituted with 1 to 3 substituents independently selected from halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, and optionally substituted 5 or 6 membered aryl or heteroaryl. $R^2$ and $R^3$ can be defined as described herein.

In some embodiments, $A^1$ can be selected from C, O, S, N, $CR^8$, $C(R^8)_2$ and $NR^9$.

In some embodiments, each $R^8$ can be independently selected from hydrogen, halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, optionally substituted 5 or 6 membered aryl or heteroaryl, and optionally two $R^8$ substituents can be joined together to form an optionally substituted 3 to 7 membered carbocyclic or heterocyclic ring. In an embodiment, each $R^8$ can be independently selected from hydrogen, halo, CN, $NO_2$, $C(O)R^2$, $OR^2$, $OS(O)_2R^2$, $NR^2R^3$, $SR^2$, $C_{1-10}$alkyl, $C_{2-10}$alkenyl, $C_{2-10}$alkynyl, $C_{1-10}$alkylhalo, $C_{2-10}$alkenylhalo and $C_{2-10}$alkynylhalo. In a further embodiment, each $R^8$ can be independently selected from optionally substituted $C_{1-6}$alkyl groups, for example methyl or bromoethyl. $R^2$ and $R^3$ can be defined as described herein, including embodiments thereof.

In some embodiments, each $R^9$ can be independently selected from hydrogen, $C_{1-20}$alkyl, $C_{2-20}$alkenyl, $C_{2-20}$alkynyl, a 5 or 6 membered aryl or heteroaryl, and optionally two $R^9$ substituents can be joined together to form an optionally substituted 3 to 7 membered carbocyclic or heterocyclic ring, each of which can be optionally substituted with one or more substituents independently selected from halo, CN, $NO_2$, $C(O)R^2$, $OR^2$, $OS(O)_2R^2$, $NR^2R^3$, $SR^2$, aryl and heteroaryl. In one embodiment, each $R^9$ can be independently selected from hydrogen, optionally substituted $C_{1-20}$alkyl and optionally substituted 5 or 6 membered aryl or heteroaryl. In another embodiment, each $R^9$ can be independently selected from hydrogen and optionally substituted $C_{1-10}$alkyl. $R^2$ and $R^3$ can be defined as described herein, including embodiments thereof.

In one embodiment, for tethered compounds of Formula 1 and 2a, $A^1$ can be selected from C, N and $CR^8$. $R^8$ can be selected according to any embodiments as described herein. In another embodiment, for tethered compounds of Formula 1 and 2a, $A^1$ can be selected from C, N, C—H, C-halo, C—$C_{1-10}$alkyl, C—$C_{1-10}$haloalkyl, C—$C_{1-10}$alkoxy, C—$C_{1-10}$alkoxyhalo. In another embodiment, for tethered compounds of Formula 1 and 2a, $A^1$ is selected from C.

In an embodiment, for untethered compounds of Formula 2b, $A^1$ can be selected from O, S, N, $CR^8$, $C(R^8)_2$ and $NR^9$. $R^8$ and $R^9$ can be selected according to any embodiments as described herein. In another embodiment, for untethered compounds of Formula 2b, $A^1$ can be selected from O, S, N, C—H, C-halo, C—$C_{1-10}$alkyl, C—$C_{1-10}$haloalky, C—$C_{1-10}$alkoxy, C—$C_{1-10}$alkoxyhalo. In another embodiment, for untethered compounds of Formula 2b, $A^1$ is selected from C—H.

D is a donor atom that in some cases can be selected from N, O, S, P, Se and Te. In one embodiment, D is selected from N, for example wherein A is an optionally substituted pyridine group. In some embodiments, D is O. In some embodiments, D is S. In some embodiments, D is P. In some embodiments, D is Se. In some embodiments, D is Te.

In another embodiment, compounds of Formula 1 may be provided by compounds according to Formula 1a(i) or Formula 1a(ii):

Formula 1a(i)

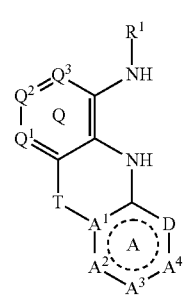

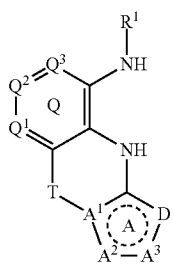

Formula 1a(ii)

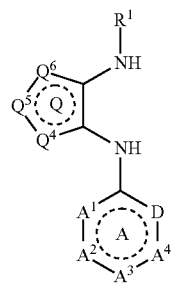

Formula 2b(i)

wherein Q, $Q^1$, $Q^2$, $Q^3$, T, D, $R^1$, $R^4$, $R^8$ and $R^9$, can be defined according to any embodiments as described herein;

A is a 5 or 6 membered heterocyclic ring containing a donor atom D and a ring atom $A^1$, wherein the dashed circle in ring A indicates one or more optional (unsaturated) double bonds;

$A^1$ is selected from C, N and $CR^8$; and $A^2$, $A^3$ and $A^4$, are each independently selected from O, S, N, $CR^8$, $C(R^8)_2$ and $NR^9$.

In another embodiment, compounds of Formula 2a may be provided by compounds according to Formula 2a(i) or Formula 2(a)(ii):

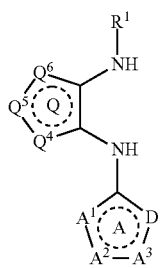

Formula 2b(ii)

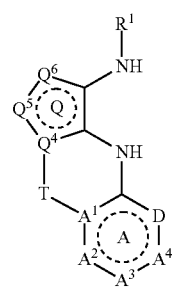

Formula 2a(i)

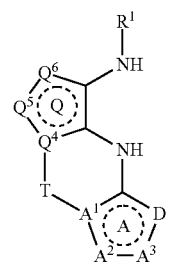

Formula 2a(ii)

wherein Q, $Q^4$, $Q^5$, $Q^6$, T, D, $R^1$, $R^4$, $R^8$ and $R^9$, can be defined according to any embodiments as described herein;

A is a 5 or 6 membered heterocyclic ring containing a donor atom D and a ring atom $A^1$, wherein the dashed circle in ring A indicates one or more optional (unsaturated) double bonds;

$A^1$ is selected from C, N and $CR^8$; and $A^2$, $A^3$ and $A^4$, are each independently selected from O, S, N, $CR^8$, $C(R^8)_2$ and $NR^9$.

In another embodiment, compounds of Formula 2b may be provided by compounds according to Formula 2b(i) or Formula 2(b)(ii):

wherein Q, $Q^4$, $Q^5$, $Q^6$, D, $R^1$, $R^4$, $R^8$ and $R^9$, can be defined according to any embodiments as described herein;

A is a 5 or 6 membered heterocyclic ring containing a donor atom D and a ring atom $A^1$, wherein the dashed circle in ring A indicates one or more optional (unsaturated) double bonds; and $A^1$, $A^2$, $A^3$ and $A^4$, are each independently selected from O, S, N, $CR^8$, $C(R^8)_2$ and $NR^9$.

In another embodiment, for compounds of Formula 1a(i), Formula 1a(ii), Formula 2a(i), Formula 2a(ii), Formula 2b(i) and Formula 2b(ii), respectively, $A^1$, $A^2$, $A^3$ and $A^4$, can each be independently defined as described above, including embodiments thereof.

In a further embodiment, for compounds of Formula 1a(i), Formula 2a(i) and Formula 2b(i), as described above, at least two of $A^1$, $A^2$, $A^3$ and $A^4$, are each independently selected from C and $CR^8$. In another embodiment, at least three of $A^1$, $A^2$, $A^3$ and $A^4$, are each independently selected from C and $CR^8$. In another embodiment, $A^1$, $A^2$, $A^3$ and $A^4$, are each independently selected from C and $CR^8$. $R^8$ can be defined according to any embodiments described herein.

In a further embodiment, for compounds of Formula 1a(ii), Formula 2a(ii) and Formula 2b(ii) as described above, at least one of $A^1$, $A^2$ and $A^3$, is selected from C and $CR^8$. In another embodiment, at least two of $A^1$, $A^2$ and $A^3$, are each independently selected from C and $CR^8$. In another embodiment, $A^1$, $A^2$ and $A^3$, are each independently selected from C and $CR^8$.

Specific examples of the A ring according to compounds of Formula 1a(i), wherein the donor atom D is N and $A^1$ is C or CH, are provided as follows:

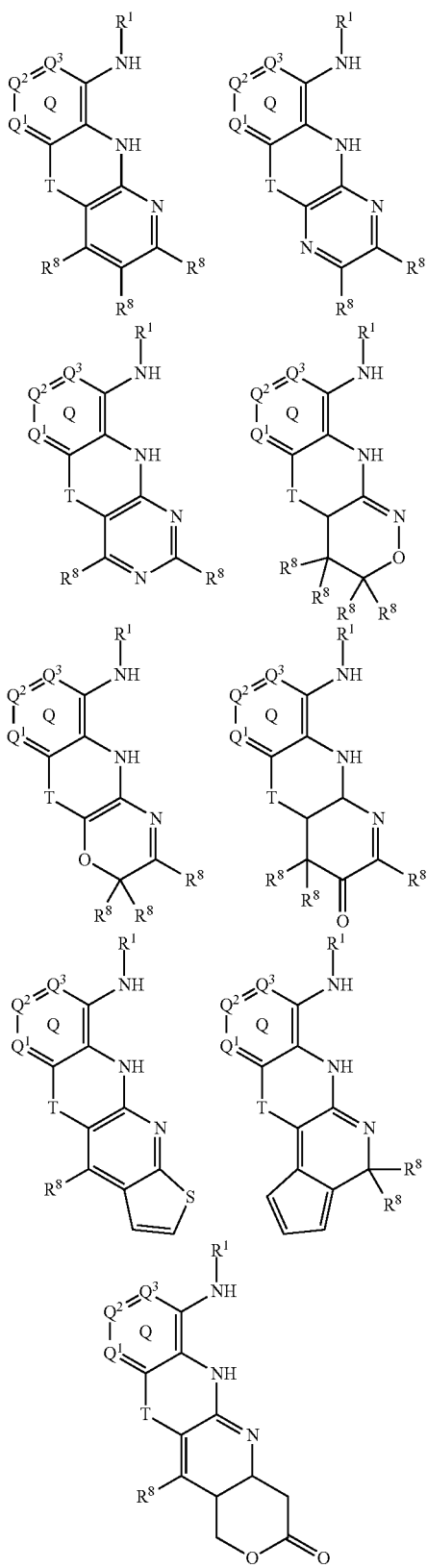

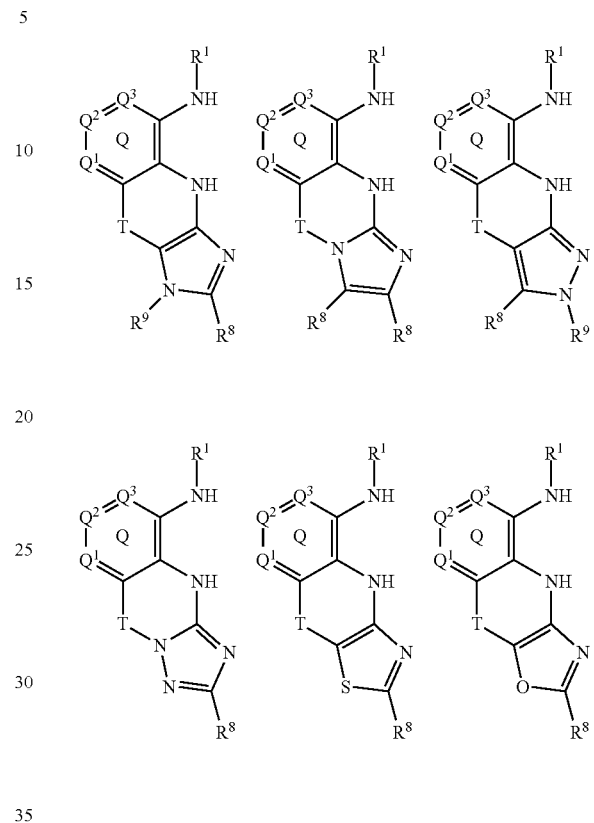

Specific examples of the A ring according to compounds of Formula 1a(ii), wherein the donor atom D is N and $A^1$ is C or N, are provided as follows:

wherein Q, $Q^1$, $Q^2$, $Q^3$, T, $R^1$, $R^8$ and $R^9$, can be defined as described herein, including any embodiments thereof as described herein.

It will be appreciated that the above specific examples of the A ring according to compounds of Formula 1a(i) and Formula 1a(ii) may also be provided as embodiments of the A ring for compounds of Formula 2a(i) and Formula 2a(ii), respectively.

Specific examples of the A ring according to compounds of Formula 2b(i), wherein the donor atom D is N and $A^1$ is $CR^8$ or $C(R^8)_2$, are provided as follows:

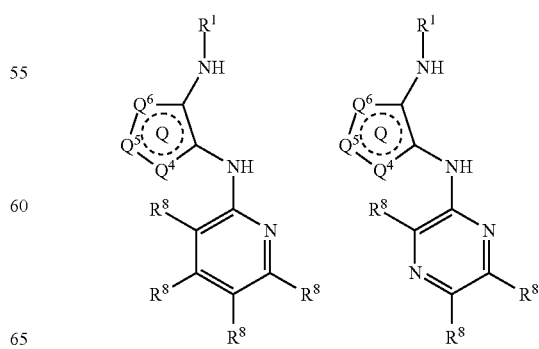

wherein Q, $Q^1$, $Q^2$, $Q^3$, T, $R^1$, $R^8$ and $R^9$, can be defined as described herein, including any embodiments thereof as described herein.

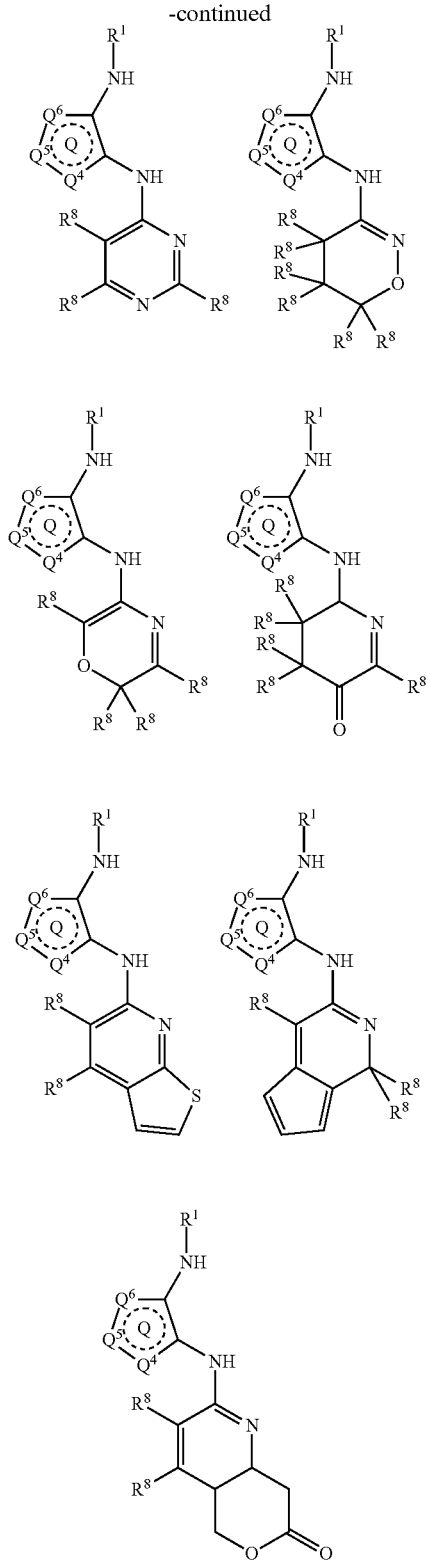

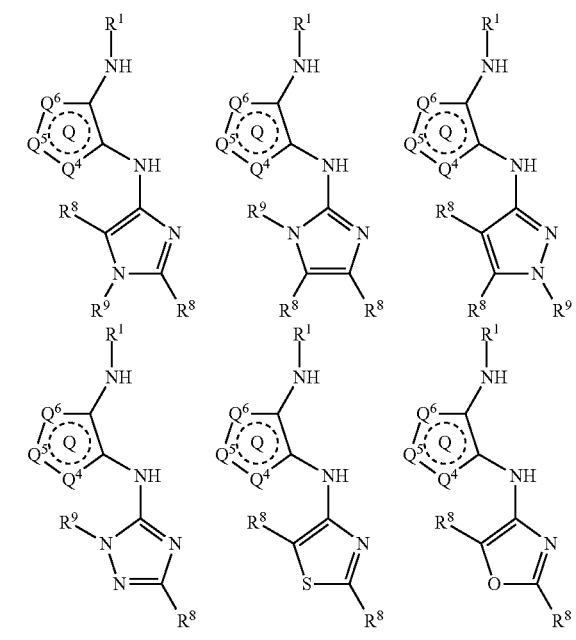

wherein Q, Q⁴, Q⁵, Q⁶, T, R¹, R⁸ and R⁹, can be defined as described herein, including any embodiments thereof as described herein.

The compounds described herein may include salts, solvates, hydrates, isomers, tautomers, racemates, stereoisomers, enantiomers or diastereoisomers of those compounds.

Diazaborole Compounds

The present disclosure also relates to diazaborole compounds of Formula 3 or Formula 4 as described below:

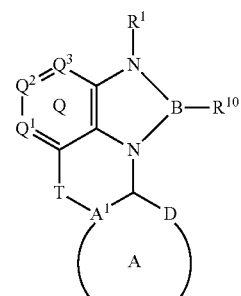

Formula 3

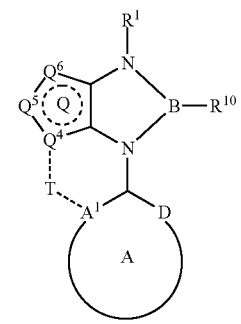

Formula 4 wherein Q, Q⁴, Q⁵, Q⁶, T, R¹, R⁸ and R⁹, can be defined as described herein, including any embodiments thereof as described herein.

Specific examples of the A ring according to compounds of Formula 2b(ii), wherein the donor atom D is N and A¹ is CR⁸ or NR⁹, are provided as follows:

wherein R¹, Q, Q¹, Q², Q³ Q⁴, Q⁵, Q⁶, T, A, A¹ and D, are as described herein and R¹⁰ is selected from hydrogen or halo.

The diazaborole compounds may be prepared from the diamine precursor compounds of Formula 1 and 2 as described herein. Processes may comprise reacting the diamine precursor compounds with boron agents, such as boron tribromide, in a solvent system, such as ether. It will be appreciated that once the diamine precursor compounds of Formula 1 and 2 are prepared, then methods of preparing boron compounds according to Formula 3 and Formula 4 using the precursor compounds would be readily known to a person skilled in the field.

In an embodiment, the diazaborole compounds of Formula 4 may be selected from a diazaborole compound of Formula 4a or Formula 4b as described below:

Formula 4a

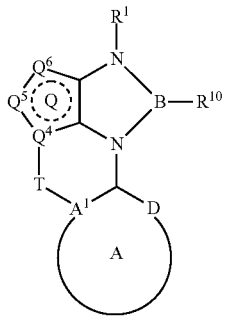

Formula 4b

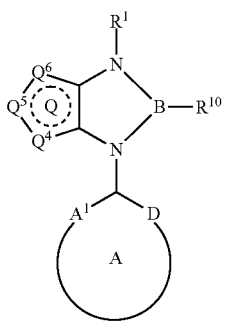

wherein $R^1$, Q, $Q^1$, $Q^2$, $Q^3$ $Q^4$, $Q^5$, $Q^6$, T, A, $A^1$ and D, are as described herein and $R^{10}$ is selected from hydrogen or halo.

It will be appreciated that any of the embodiments described herein for groups $R^1$, Q, $Q^1$, $Q^2$, $Q^3$ $Q^4$, $Q^5$, $Q^6$, T, A, $A^1$ and D, in relation to Formula 1 may also apply to compounds of Formula 3, and in relation to Formula 2a and 2b may also apply to compounds of Formula 4a and Formula 4b, respectively.

Diazaborole Metal Complexes

The present disclosure also relates to a metal complex of Formula 5 or Formula 6 as described below:

Formula 5

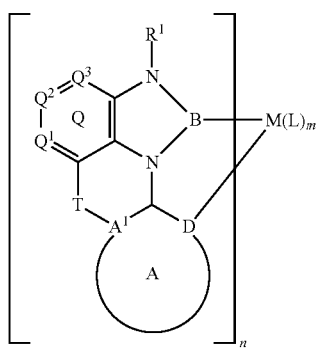

-continued

Formula 6

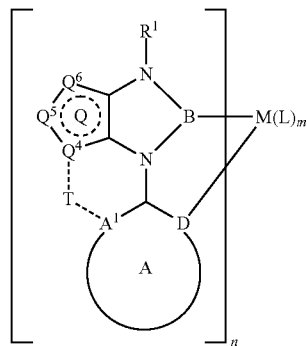

wherein
M is a metal atom selected from Ir, Pt, Rh, Pd, Ru and Os;
n is an integer selected from 1, 2 and 3;
m is an integer selected from 0, 1, 2, 3, 4, and 5;
L is a monodentate or bidentate ligand; and
$R^1$, Q, $Q^1$, $Q^2$, $Q^3$ $Q^4$, $Q^5$, $Q^6$, T, A, $A^1$ and D, are as described herein.

In an embodiment, the metal complex of Formula 6 may be selected from a metal complex of Formula 6a or Formula 6b as described below:

Formula 6a

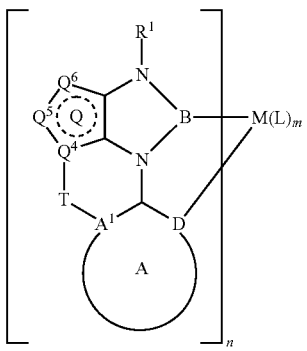

Formula 6b

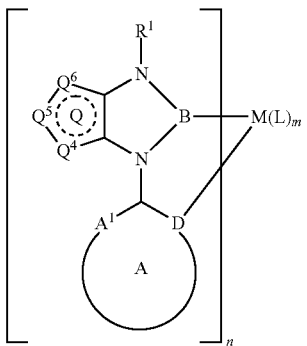

wherein
M is a metal atom selected from Ir, Pt, Rh, Pd, Ru and Os;
n is an integer selected from 1, 2 and 3;
m is an integer selected from 0, 1, 2, 3, 4, and 5;
L is a monodentate or bidentate ligand; and
$R^1$, Q, $Q^1$, $Q^2$, $Q^3$ $Q^4$, $Q^5$, $Q^6$, T, A, $A^1$ and D, are as described herein.

It will be appreciated that any of the embodiments described herein for groups $R^1$, Q, $Q^1$, $Q^2$, $Q^3$ $Q^4$, $Q^5$, $Q^6$, T, A, $A^1$ and D, in relation to Formula 1 may also apply to compounds of Formula 5, and in relation to Formula 2a and 2b may also apply to compounds of Formula 6a and Formula 6b, respectively.

The metal complexes described herein may include salts, solvates, hydrates, isomers, tautomers, racemates, stereoisomers, enantiomers or diastereoisomers of those complexes. The transition metal M may also have different coordination and/or oxidation states. The coordination number of a metal complex refers to the number of ligands (i.e. donor atoms) attached to the metal. A metal may be coordinated to one or more ligands by interactions of the metal's d orbital with the s or p orbitals of the ligand(s). For example, typical oxidation states for Pt are +2 and +4, and Pt is typically coordinated to 4 or 6 ligands depending on the type of ligands. The geometries of metal complexes may also vary, for example Pt is typically square planar when coordinated to 4 ligands and octahedral when coordinated to 6 ligands, although the geometries will depend on the type of metal and coordinated ligands. Common oxidation states for Ir are +3 and +4, and Ir is in some cases hexacoordinate.

Integer ranges for "n" and "m" can be selected so that the coordination number on the metal M in total corresponds, depending on the metal, to the usual coordination number for this metal. As mentioned above, it is generally known that metal coordination compounds have different coordination numbers depending on the metal and on the oxidation state of the metal, i.e. bond a different number of ligands. Since the preferred coordination numbers of metals and metal ions in various oxidation states are part of the general knowledge of the person skilled in the art in the area of organometallic chemistry or coordination chemistry, it is straightforward for the person skilled in the art to use a suitable type and number of ligands L, depending on the metal and its oxidation state, and in view of diamine compound of Formula 1 and 2 providing at least a bidentate ligand in itself, and thus to make a suitable choice of n and m.

For example, it will be appreciated that the diamine compounds of Formula 1 and 2 provide at least one bidentate ligand (two donor atoms as ligands) to the metal M. Consequently, where n is 1 and the coordination number of the metal is 6, then an additional 4 donor atoms to M are required by (L)m, which can be provided by 4 monodentate ligands, or 2 bidentate ligands, or a combination thereof.

In one embodiment, M is a metal atom selected from Ir and Pt. In some embodiments, M is Ir. In some embodiments, M is Pt. In some embodiments, M is Rh. In some embodiments, M is Pd. In some embodiments, M is Ru. In some embodiments, M is Os.

The metal complex may be homoleptic, for example containing the same ligands where m is 0, L is absent and n is an integer selected from 1, 2, and 3. In one embodiment, M is Pt, n is 2, m is 0 and L is absent. In another embodiment, M is Ir, n is 3, m is 0 and L is absent.

The metal complex may be heteroleptic, for example containing at least one ligand L. In one embodiment, M is Ir, n is 2, and m is an integer selected from 1 and 2, wherein m and L are selected to provide 2 donor atoms as ligands to M. It will be appreciated that the 2 donor atoms from L may be provided by L being 2 monodentate ligands, such as Cl, or by L being a single bidentate ligand, such as ethylenediamine.

Additional Ligands

Any convenient ligands may be utilized in the subject metal complexes. In some cases, the ligand L may be a neutral or monoanionic, monodentate or bidentate ligand.

A neutral, monodentate ligand L may be independently selected from carbon monoxide, NO, isonitriles, such as, for example, tert-butyl isonitrile, cyclohexyl isonitrile, adamantyl isonitrile, phenyl isonitrile, mesityl isonitrile, 2,6-dimethylphenyl isonitrile, 2,6-diisopropylphenyl isonitrile, 2,6-di-tert-butylphenyl isonitrile, amines, such as, for example, trimethylamine, triethylamine, morpholine, phosphines, such as, for example, trifluorophosphine, trimethylphosphine, tricyclohexylphosphine, tri-tert-butylphosphine, triphenylphosphine, tris(pentafluorophenyl)phosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, and nitrogen-containing heterocycles, such as, for example, pyridine, pyridazine, pyrazine, pyrimidine, triazine.

A monoanionic, monodentate ligand L may be independently selected from hydride, deuteride, the halides F, Cl, Br and I, alkylacetylides, such as, for example, methyl-C≡C—, tert-butyl-C≡C—, aryl- and heteroarylacetylides, such as, for example, phenyl-C≡C—, cyanide, cyanate, isocyanate, thiocyanate, isothiocyanate, aliphatic or aromatic alcoholates, such as, for example, methanolate, ethanolate, propanolate, isopropanolate, tert-butylate, phenolate, aliphatic or aromatic thioalcoholates, such as, for example, methanethiolate, ethanethiolate, propanethiolate, isopropanethiolate, tert-butanethiolate, thiophenolate, amides, such as, for example, dimethylamide, diethylamide, diisopropylamide, morpholide, carboxylates, such as, for example, acetate, trifluoroacetate, propionate, benzoate, and anionic, nitrogen-containing heterocycles, such as pyrrolide, imidazolide, pyrazolide. The alkyl groups in these groups may be $C_{1-20}$alkyl groups, $C_{1-10}$alkyl groups, or $C_{1-4}$alkyl groups. These groups and the aryl and heteroaryl groups are as defined above.

Di- or trianionic, monodentate ligand L may be independently selected from $O_2^-$, $S_2^-$, nitrenes, which result in coordination in the form R—N=M, where R generally stands for a substituent, or $N_3$—.

A neutral or mono- or dianionic, bidentate ligand L may be independently selected from diamines, such as, for example, ethylenediamine, N,N,N',N'-tetramethylethylenediamine, propylenediamine, N,N,N',N'-tetramethylpropylenediamine, cis- or trans-diaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-diisopropylphenylimino)ethyl]pyridine, 2-[1-(methylimino)ethyl]-pyridine, 2-[1-(ethylimino)ethyl]pyridine, 2-[1-(isopropylimino)ethyl]pyridine, 2-[1-(tert-butylimino)ethyl]pyridine, diimines, such as, for example, 1,2-bis-(methylimino)ethane, 1,2-bis(ethylimino)ethane, 1,2-bis(isopropylimino)ethane, 1,2-bis(tert-butylimino)ethane, 2,3-bis(methylimino)butane, 2,3-bis-(ethylimino)butane, 2,3-bis(isopropylimino)butane, 2,3-bis(tert-butylimino)butane, 1,2-bis(phenylimino)ethane, 1,2-bis(2-methylphenylimino) ethane, 1,2-bis(2,6-diisopropylphenylimino)ethane, 1,2-bis(2,6-di-tert-butylphenylimino)ethane, 2,3-bis(phenylimino) butane, 2,3-bis(2-methylphenylimino)butane, 2,3-bis(2,6-diisopropylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis(diphenylphosphino)methane, bis(diphenylphosphino)ethane, bis(diphenylphosphino)propane, bis(dimethylphosphino)methane, bis(dimethylphosphino)ethane, bis(dimethylphosphino)propane, bis(diethylphosphino)methane, bis(diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

A bidentate monoanionic ligand L may be selected which, with the metal, form a cyclometallated five-membered ring having at least one metal-carbon bond. These are, in particular, ligands as are generally used in the area of phosphorescent metal complexes for organic electroluminescent devices, i.e. ligands of the phenylpyridine, naphthylpyridine, phenylquinoline, phenylisoquinoline, etc., type, each of which may be substituted by one or more radicals.

Emission Materials & Electronic Devices

The complexes of Formula 5, Formula 6a and Formula 6b, as described herein including embodiments thereof as described herein, can be used as an active component in an electronic device.

Electronic devices may be selected from the group consisting of organic electroluminescent devices (OLEDs), organic field-effect transistors (O-FETs), organic thin-film transistors (O-TFTs), organic light-emitting transistors (O-LETs), organic integrated circuits (G-ICs), organic solar cells (O-SCs), organic field-quench devices (O-FQDs), light-emitting electrochemical cells (LECs), organic photoreceptors and organic laser diodes (O-lasers). In one embodiment, the electronic device is an organic electroluminescent device.

Active components are generally the organic, organometallic or inorganic materials introduced between the anode and cathode, for example charge-injection, charge-transport or charge-blocking materials, but in particular emission materials and matrix materials. The metal complexes of Formula 5, Formula 6a or Formula 6b, as described herein including embodiments thereof as described herein, can exhibit particularly good properties for these functions, in particular as an emission material in organic electroluminescent devices, as described in further detail below. Organic electroluminescent devices are therefore a particular embodiment of the present disclosure.

The organic electroluminescent device can comprise a cathode, an anode and at least one emitting layer (which may also be referred to as an emissive layer). The metal complexes of Formula 5, Formula 6a or Formula 6b, can be provided as an emitting compound in the emitting layer. The metal complexes of Formula 5, Formula 6a or Formula 6b, may also be provided as a matrix material for an emitting compound in the emitting layer.

The organic electronic device may comprise further layers, selected from in each case one or more hole-injection layers, hole-transport layers, hole-blocking layers, electron-transport layers, electron-injection layers, electron-blocking layers, exciton-blocking layers, charge-generation layers and/or organic or inorganic p/n junctions.

Optional interlayers may be added to provide, for example, an exciton-blocking function, to be introduced between two emitting layers or also between other layers. The OLED may comprise one or more emitting layers, where at least one emitting layer comprises at least one metal complex of Formula 5, Formula 6a and Formula 6b. If a plurality of emission layers are present, these can have in total a plurality of emission maxima between 380 nm and 750 nm, resulting overall in white emission, i.e. various emitting compounds which are able to fluoresce or phosphoresce are used in the emitting layers. There may be provided a three-layer system, where the three layers exhibit blue, green and orange or red emission, for example in accordance with WO05/011013.

In one embodiment, the electronic device comprises at least one metal complex of Formula 5, Formula 6a and Formula 6b, as an emitting compound in an emitting layer. Each of the one or more layers in the device may comprise one or more matrix materials. The mixture of the metal complexes of the Formula 5, Formula 6a and Formula 6b, and the matrix material may comprise between 1 and 99% by vol., between 2 and 90% by vol., between 3 and 40% by vol., or between 5 and 15% by vol., of the metal complex, based on the mixture as a whole comprising emitter and matrix material. Correspondingly, the mixture may comprise between 99 and 1% by vol., between 98 and 10% by vol., between 97 and 60% by vol., or between 95 and 85% by vol., of the matrix material, based on the mixture as a whole comprising emitter and matrix material.

Suitable matrix materials may include ketones, phosphine oxides, sulfoxides and sulfones, for example in accordance with WO04/013080, WO04/093207 or WO06/005627, triarylamines, carbazole derivatives, for example CBP (N,N-biscarbazolylbiphenyl), mCBP or the carbazole derivatives disclosed in WO05/039246, US2005/0069729, JP2004/288381, EP1205527 or WO08/086851, indolocarbazole derivatives, for example in accordance with WO07/063754 or WO08/056746, azacarbazoles, for example in accordance with EP1617710, EP1617711, EP1731584, JP2005/347160, bipolar matrix materials, for example in accordance with WO07/137725, silanes, for example in accordance with WO 05/111172, azaboroles or boronic esters, for example in accordance with WO06/117052, triazine derivatives, for example in accordance with WO07/063754 or WO08/056746, or zinc complexes, for example in accordance with EP652273 or WO09/062578. The metal complexes of Formula 5, Formula 6a and Formula 6b, may also be suitable as matrix materials. In general, all matrix materials as employed in accordance with the prior art for phosphorescent emitters in organic electroluminescent devices can also be employed for the compounds according to the present disclosure. Mixtures of these matrix materials may also be used.

The electroluminescent device may comprise a separate hole-transport layer or comprise a metal complex, which is identical or similar to the complex employed in the emitting layer, as hole-transport material in the hole-transport layer.

The metal complexes of Formula 5, Formula 6a and Formula 6b, including embodiments as described herein, may be employed as a matrix material for an emitting compound in an emitting layer.

The electroluminescent device may comprise a matrix material and at least two phosphorescent emitters in the emitting layer, where at least one of the two phosphorescent emitters is a metal complex of Formula 5, Formula 6a or Formula 6b. The phosphorescent emitter which emits at shorter wavelength serves here as matrix for the phosphorescent emitter which emits at longer wavelength. The metal complex of Formula 5, Formula 6a and Formula 6b, may be the compound emitting at shorter wavelength or the compound emitting at longer wavelength. Likewise, both phosphorescent compounds can be a metal complex of Formula 5, Formula 6a and Formula 6b.

If the metal complexes of Formula 5, Formula 6a and Formula 6b are employed as matrix material for an emitting compound in an emitting layer, they can be provided in combination with one or more phosphorescent materials (triplet emitters) or fluorescent materials (singlet emitters). For the purposes of the present disclosure, phosphorescence is taken to mean the luminescence from an excited state of relatively high spin multiplicity, i.e. a spin state>1, in particular from an excited triplet state or from an MLCT mixed state. For the purposes of the present disclosure, all luminescent transition-metal complexes, in particular all luminescent iridium and platinum complexes, are regarded as phosphorescent materials. The mixture of the metal complexes of Formula 5, Formula 6a and Formula 6b, as described herein, and the emitting compound can comprise between 99 and 1% by vol., 98 and 10% by vol., between 97 and 60% by vol., or between 95 and 85% by vol., of the metal complex, based on the mixture as a whole comprising emitter and matrix material. Correspondingly, the mixture comprises between 1 and 99% by vol., between 2 and 90% by vol., between 3 and 40% by vol., between 5 and 15% by vol., of the emitter, based on the mixture as a whole comprising emitter and matrix material. A metal complex of Formula 5, Formula 6a and Formula 6b, may be used in combination with another compound or complex as the matrix material.

The phosphorescence emitters used may be selected from compounds which contain copper, molybdenum, tungsten, rhenium, ruthenium, osmium, rhodium, iridium, palladium, platinum, silver, gold or europium, in particular compounds which contain iridium or platinum. Examples of the emitters described above are described in WO00/70655, WO01/41512, WO02/02714, WO02/15645, EP1191613, EP1191612, EP1191614, WO05/033244 or WO09/118087.

The metal complexes of Formula 5, Formula 6a and Formula 6b, as described herein, may be used as hole-blocking materials in a hole-blocking layer and/or as electron-transport material in an electron-transport layer. The emitting layer may be fluorescent or phosphorescent.

Each of the one or more layers in the organic electroluminescent device may be prepared by a sublimation process or by organic vapour phase deposition process, such as organic vapour jet printing (see M. S. Arnold et al., *Appl. Phys. Lett.* 2008, 92, 053301). Each of the one or more layers in the organic electroluminescent device may be produced from solution, such as, for example, by spin coating, or by means of any desired printing process, such as, for example, screen printing, flexographic printing, offset printing, LITI (light induced thermal imaging, thermal transfer printing), ink-jet printing or nozzle printing. Hybrid processes, in which one or more layers are applied from solution and one or more other layers are applied by vapour deposition, are also possible.

In some embodiments, the metal complexes of Formula 5, Formula 6a and Formula 6b, as described herein, may be used in combination with one or more of a hole injection material, a hole transporting compound (or material), an electron transporting compound and/or an additional emission compound, examples of which may include the following:

Exemplary hole transporting materials/compounds include:

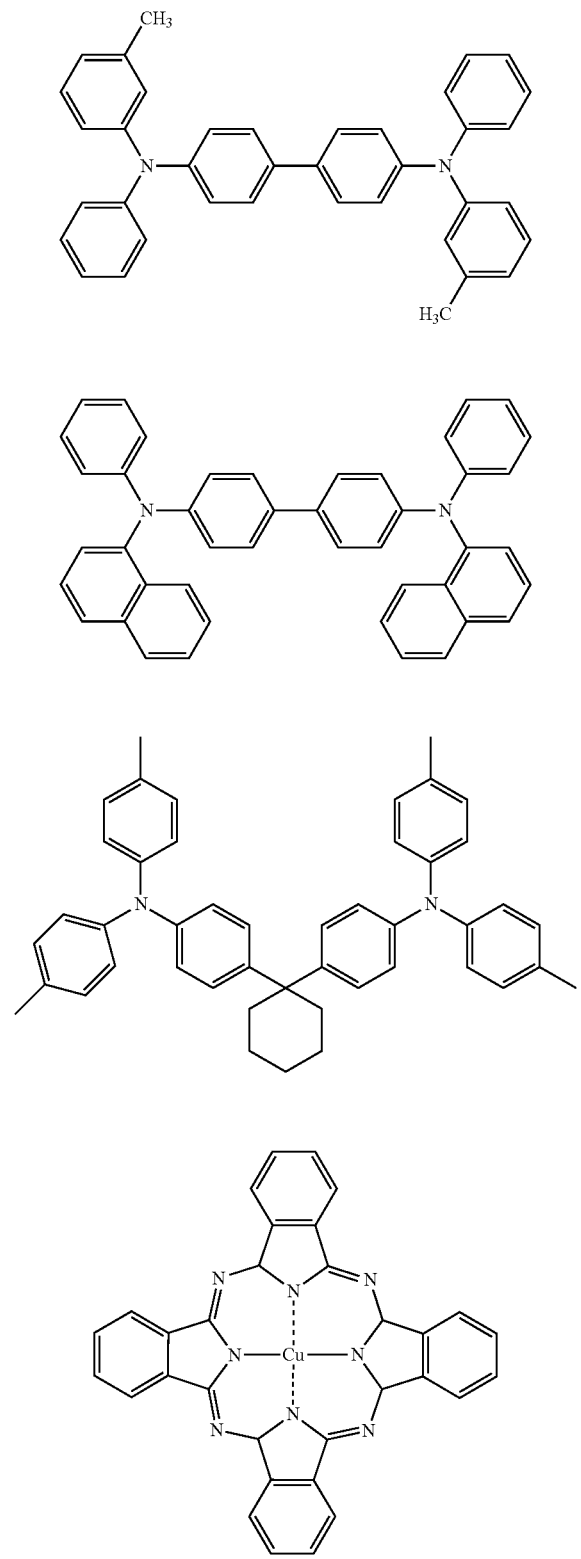

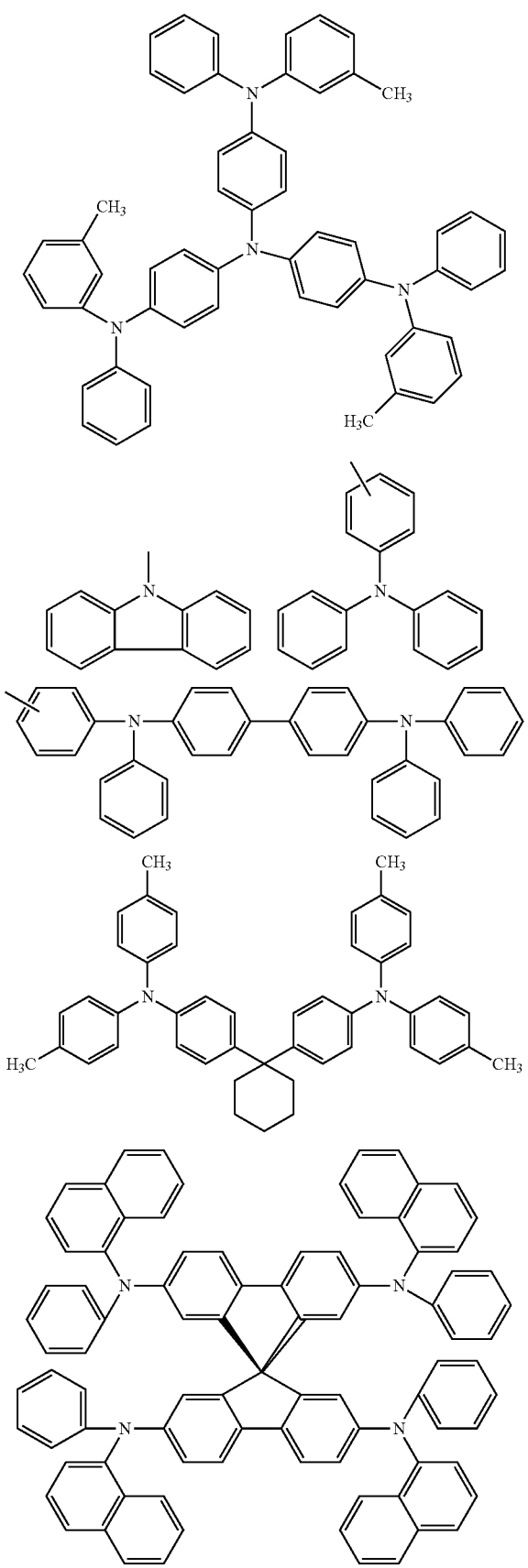
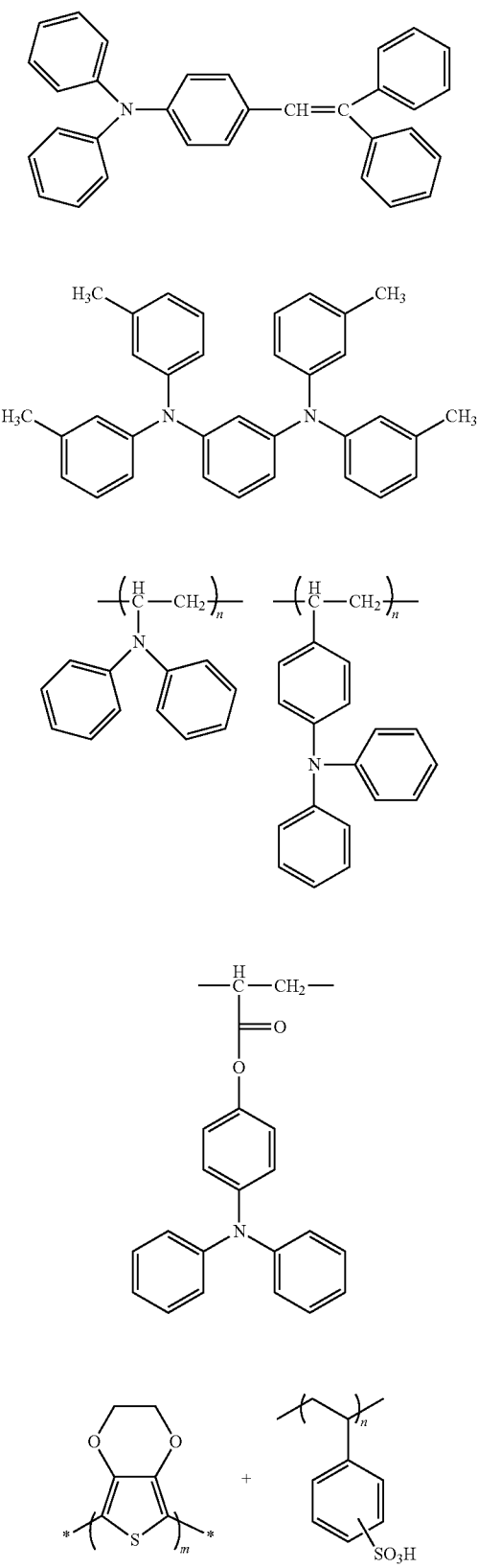
Exemplary electron transporting materials/compounds include:

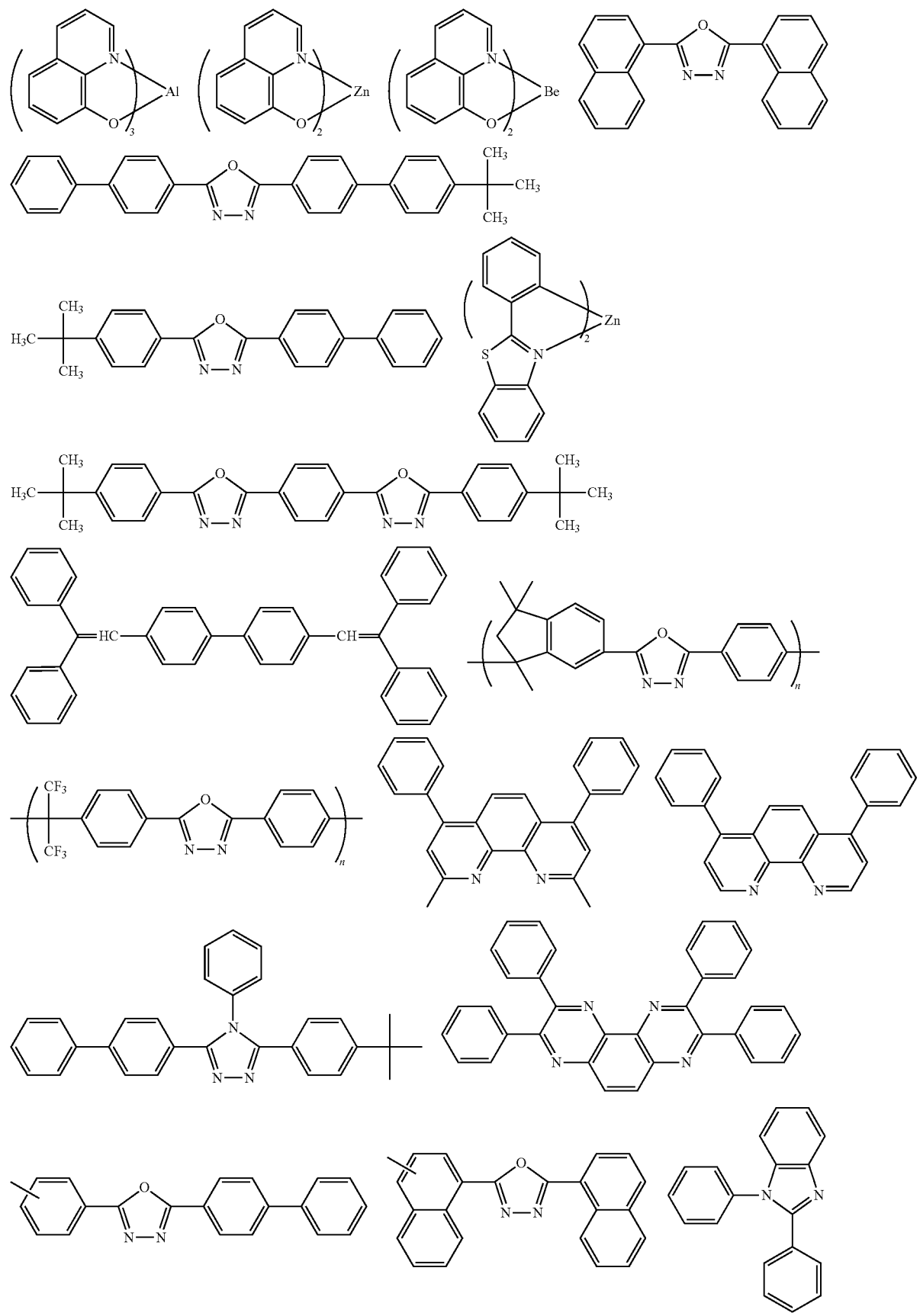

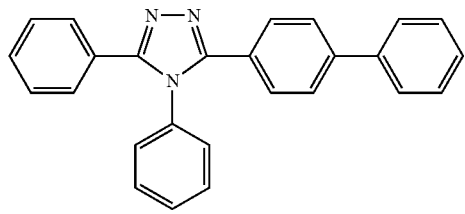 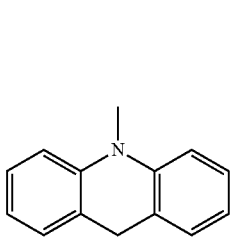 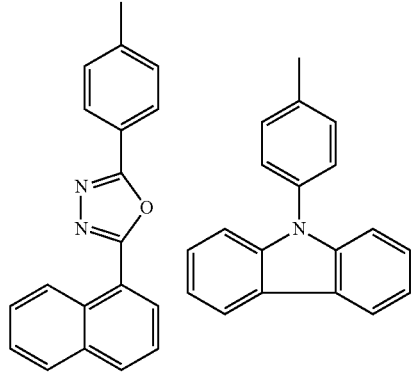

The anode is typically selected form a material having a large work function, examples of which may include metals, such as gold, platinum, nickel, palladium, cobalt, selenium, vanadium and their alloys; metal oxides, such as tin oxide, zinc oxide, indium zinc oxide (IZO) and indium tin oxide (ITO) and electroconductive polymers, such as PEDOT: PSS, polyaniline, polypyrrole and polythiophene and derivatives thereof. These compounds may be used singly or in combination of two or more species. A substrate for the anode of the organic electroluminescence device may be provided and selected from an opaque substrate made from any suitable material, such as metal or ceramics, or a transparent substrate made from any suitable transparent material such as glass, quartz, plastics.

The cathode is typically selected from a material having a smaller work function, usually under 4.0 eV, examples of which may include; metals such as sodium, magnesium, calcium, lithium, potassium, aluminium, indium, silver, lead, chromium and their alloys, or oxides.

A charge blocking layer may be deposited adjacent to either electrode to avoid current leakage. The charge blocking material may be an inorganic compound, examples of which may include aluminium oxide, lithium fluoride, lithium oxide, caesium oxide, magnesium oxide, magnesium fluoride, calcium oxide, calcium fluoride, aluminium nitride, titanium oxide, silicon oxide, silicon nitride, boron nitride, vanadium oxide.

The one or more organic layers in the electronic device may be constituted by:

a single layer doped with a phosphorescent material of the present application;

multiple layers of which at least one layer may be doped with a phosphorescent material of the present application; or multiple layers of which at least one layer may be comprised entirely of a phosphorescent material of the present application.

Further examples of the device structure may be provided as follows:

anode/emissive layer/cathode;
anode/electron transport layer/cathode;
anode/hole transporting layer/emissive layer/electron transporting layer/cathode;
anode/hole injection layer/hole transporting layer/emissive layer/electron transporting layer/cathode;
anode/hole transporting layer/emission layer/electron transporting layer/electron injection layer/cathode;
anode/hole injection layer/emission layer/electron transporting layer/electron injection layer/cathode;
anode/charge blocking layer/hole transporting layer/emission layer/electron transporting layer/cathode;
anode/hole transporting layer/emission layer/electron transporting layer/charge blocking layer/cathode;
anode/inorganic semiconductor/charge blocking layer/hole transporting layer/emission layer/charge blocking layer/cathode;
anode/charge blocking layer/hole transporting layer/emission layer/electron transporting layer/charge blocking layer/cathode;
anode/charge blocking layer/hole injection layer/hole transporting layer/emission layer/electron transporting layer/electron injection layer/cathode; or
anode/charge blocking layer/hole injection layer/hole transporting layer/emission layer/electron transporting layer/electron injection layer/charge blocking layer/cathode.

Synthesis of Compounds and Metal Complexes

The compounds and complexes of Formula 1-6 can be prepared by various processes, but where the processes described below have proven particularly suitable.

It will be appreciated that the diamine compounds of Formula 1 and 2 can be precursor compounds for the diazaborole compounds of Formula 3 and 4, respectively, and for the metal complexes of Formula 5 and 6, respectively.

A general process for preparing the diamine compounds of Formula 1 and 2 may comprise:

reacting an optionally substituted heterocyclic compound comprising a fused imidazole group (e.g. Q group as defined herein) with an optionally substituted monocyclic or bicyclic 5 or 6 membered heterocyclic ring comprising a donor atom D selected from N, O, S, P, Se and Te (e.g. A group as defined herein), to form an imidazyl N-substituted heterocyclic compound; and reacting the imidazyl N-substituted heterocyclic compound with a reducing agent to form a diamine compound of Formula 1 or Formula 2, as described herein.

An example of a suitable reducing agent is a bulky (i.e. sterically hindered) reducing agent such as DIBAL-H. Other suitable reducing agents will be well known to persons skilled in the field, such as LiAlH$_4$.

The metal complexes of Formula 5 and 6, as described herein, may be prepared by the following general process:

reacting a diamine compound of Formula 1 or Formula 2 with a boron agent to obtain a diazaborole compound of Formula 3 or Formula 4, respectively, as described herein;

reacting the compound of Formula 3 or Formula 4 with a precursor complex of the metal M having substitutable ligands in a ratio suitable to obtain a product being a metal complex of Formula 5 or Formula 6 having the desired number n of diamine compounds of Formula 3 or Formula 4, and optionally ligands L, being co-ordinated to the metal M; and optionally further reacting the product with another ligand L in a ratio suitable to introduce the desired number of ligands L into the metal complex of Formula 5 or Formula 6.

An example of a suitable boron agent is $BBr_3$. Other suitable boron agents will be well known to persons skilled in the field.

An example of a suitable precursor complex metal M is trispyridinoiridium trichloride. Other suitable iridium precursors will be well known to persons skilled in the field.

An example of a general scheme for preparing a metal complex of Formula 6b via a diamine compound of Formula 2b is provided as follows:

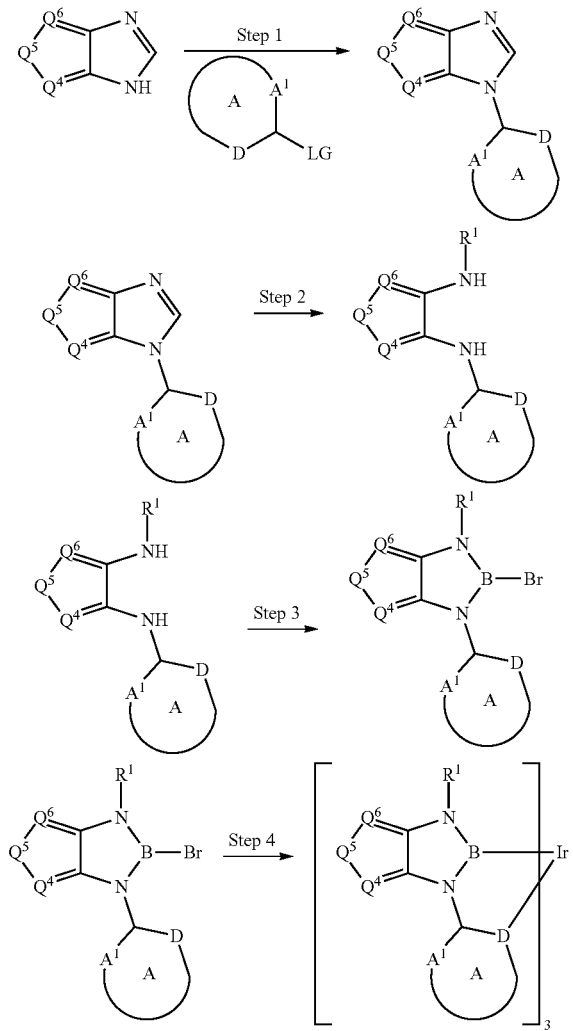

wherein $R^1$, $Q^4$, $Q^5$, $Q^6$, A, $A^1$ and D can be defined as described herein.

In various embodiments, there are provided processes for preparing compounds and complexes of Formula 2b, Formula 4b and Formula 6b, which may comprise any one or more of the general steps described in the above general scheme.

It will be appreciated that a process for preparing the diamine compounds of Formula 2b, as described herein, may comprise steps 1 and 2, or step 2 above.

The process for preparing the diazaborole compounds of Formula 4b may comprise steps 1 to 3, steps 2 and 3, or step 3 above.

The process for preparing the metal complexes of Formula 6b may comprise steps 1 to 4, steps 2 to 4, steps 3 and 4, or step 4 above.

Step 1 may comprise a substitution reaction comprising a Q ring and a leaving group LG of the A ring. Suitable reagents may include copper iodide, caesium carbonate, and dimethylformamide. A suitable leaving group (LG) may include a halogen atom.

Step 2 may comprise a reduction reaction to a diamine compound of Formula 2b. Suitable reducing agents may include a sterically hindered reducing agent such as diisobutylaluminium hydride (DIBAL-H). Suitable solvents may include toluene at elevated temperatures (110° C.) for 8 hours.

Step 3 may comprise a reaction with a boron agent to prepare the diazaborole compounds of Formula 4b. A suitable boron agent may be boron tribromide ($BBr_3$). A suitable solvent may be an ether, which can be provided at reflux conditions.

Step 4 may comprise a reaction with a metal precursor to form the metal complexes of Formula 6b. Suitable metal precursors include trispyridinoiridium.

An example of a general scheme for preparing a metal complex of Formula 5 via a diamine compound of Formula 1 is provided as follows:

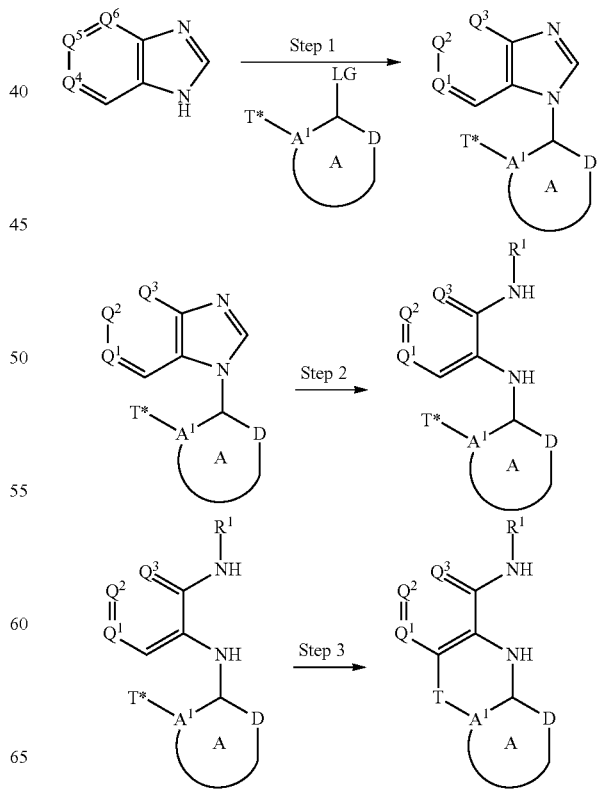

49

-continued

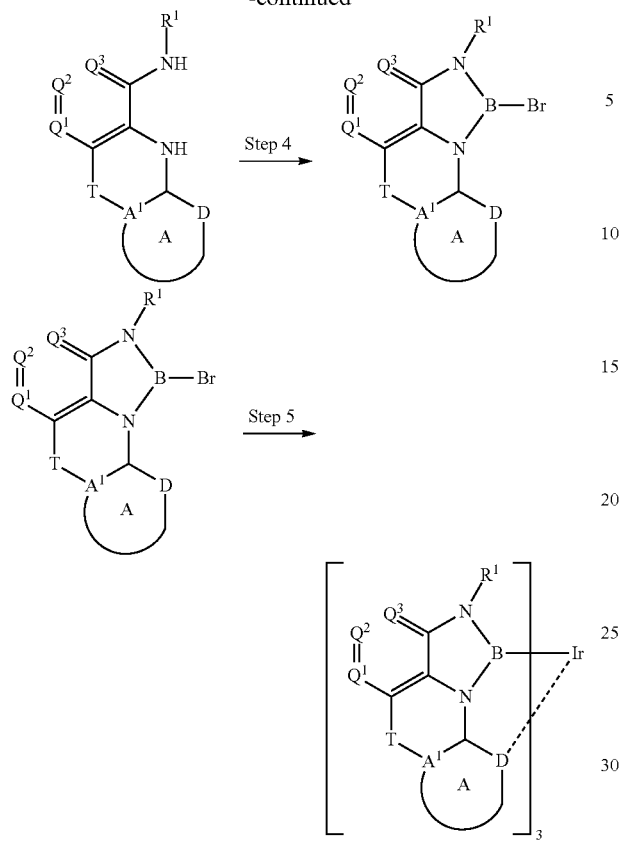

wherein $R^1$, $Q^1$, $Q^2$, $Q^3$, T, A, $A^1$ and D can be defined as described herein, wherein T* is a precursor for T.

A suitable example of T* is 2-propene. T* may be a tertiary alcohol, an acid chloride or any group that can undergo a Friedel-Crafts alkylation.

It will be appreciated that a process for preparing the diamine compounds of Formula 1, as described herein, may comprise steps 1 to 3, steps 2 and 3, or step 3 above.

The process for preparing the diazaborole compounds of Formula 3 may comprise steps 1 to 4, steps 2 to 4, steps 3 and 4, or step 4 above.

The process for preparing the metal complexes of Formula 5 may comprise steps 1 to 5, steps 2 to 5, steps 3 to 5, steps 4 and 5, or step 5 above.

Step 1 may comprise a substitution reaction of a Q ring and a leaving group LG of the A ring. Suitable reagents may include potassium carbonate. A suitable leaving group may include a halogen atom.

Step 2 may comprise a reduction reaction to a diamine compound comprising a reducing agent. Suitable reducing agents may sterically hindered reducing agents such as diisobutylaluminium hydride (DIBAL-H). Suitable solvents may include tetrahydrofuran (THF) at reflux.

Step 3 may comprise tethering the T group to the Q ring for preparing the diamine compounds of Formula 1. Suitable reagents may include phosphoric acid/acetic acid at elevated temperatures (e.g. 120° C.).

Step 4 may comprise a reaction with a boron agent to prepare the diazaborole compounds of Formula 3. A suitable boron agent may include boron tribromide ($BBr_3$). Suitable solvent include ether at reflux.

Step 5 may comprise a reaction with a metal precursor to form the metal complexes of Formula 5. A suitable metal precursor may be trispyridinoiridium.

50

In various embodiments, there are provided processes for preparing compounds and complexes of Formula 1, Formula 3 and Formula 5, which may comprise any one or more of the general steps described in the above general scheme.

EXAMPLES

The invention is further illustrated by the following examples. The examples are provided for illustrative purposes only. They are not to be construed as limiting the scope or content of the invention in any way.

Scheme 1: Synthesis of metal complex via diamine compound of Formula 2b

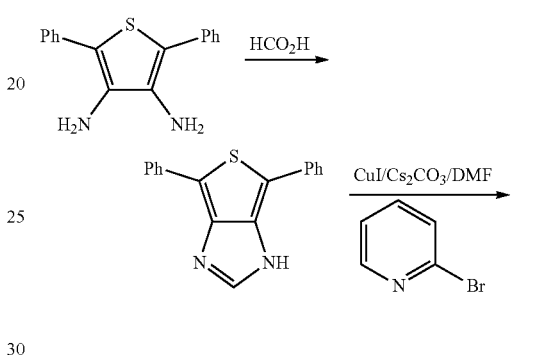

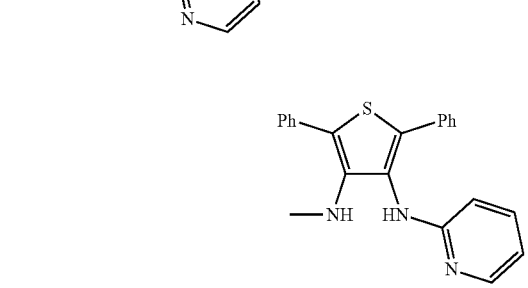

Example 1: Synthesis of Diamine Compound of Formula 2b

Synthesis of 4,6-diphenyl-1H-thieno[3,4-d]imidazole

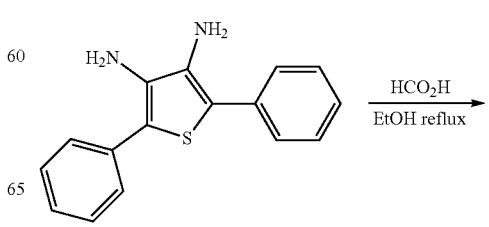

-continued

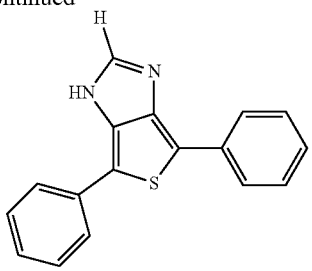

2,5-Diphenylthiophene-3,4-diamine (2.66 g, 0.01 mol) was placed into a round bottom flask with ethanol (100.0 ml). Formic acid (10.0 ml) was then added and the mixture heated at a refluxing temperature for 16 hours. After cooling, the volatiles were removed. Ethyl acetate (100.0 ml) was added to the crude mixture and the resulting precipitate filtered. The filtrate was then placed into a separatory funnel, washed (3×50.0 ml water), dried (MgSO₄), filtered and solvent removed to give an orange/red solid which was placed into a 50.0 ml solution of petroleum spirits (BP 40-60° C.) and dichloromethane (50:1). After stirring for 30 minutes at ambient temperature the mixture was filtered to give 1.09 g (41%) imidazole as a yellow solid. $H^1$-NMR (CDCl₃, 400 MHz): 9.6 (br-s, 1H), 7.98 (s, 1H), 7.76 (m, 4H), 7.36 (9t, 4H), 7.12 (t, 2H). $C^{13}$-NMR (CDCl₃, 100 MHz): 161.4, 149.9, 135.5, 134.2, 131.5, 131.0, 129.5, 129.2, 126.8, 125.8, 117.5.

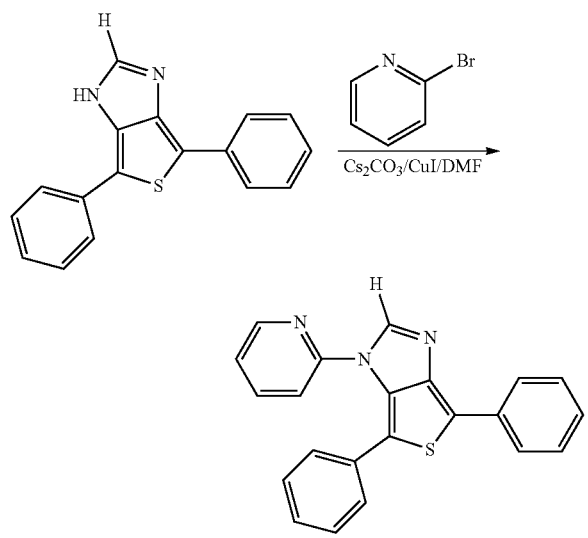

4,6-diphenyl-1-H-thieno[3,4-d]imidazole (2.76 g, 0.01 mol) was placed into a round bottom flask containing N,N-dimethylformamide (DMF, 25.0 ml). The mixture was then placed under a nitrogen atmosphere. Calcium Carbonate (3.34 g, 1.02 eq), copper iodide (483 mg, 0.0025 mol) and 2-bromopyridine (1.84 g, 0.011 mol) were added and the reaction mixture was then stirred overnight at 140° C. After cooling, the reaction mixture was diluted with ethyl acetate (250 ml), filtered and volatiles removed. The crude was pre-adsorbed onto silica and purified by chromatography. (100% petroleum (BP 40-60° C.) to 20:80 EtOAc:Petrol gradient elution) to give 1.09 g product (31%) as a yellow solid. $H^1$-NMR (CDCl₃, 400 MHz): 8.63 (s, 1H), 8.43 (m, 1H), 8.07 (d, 2H), 7.43 (t, 3H), 7.22 (m, 4H), 7.15 (d, 3H), 6.63 (d, 1H). $C^{13}$-NMR (CDCl₃, 100 MHz): 151.4, 148.9, 148.4, 137.9, 133.9, 133.3, 132.5, 131.5, 129.5, 129.1, 128.2, 127.6, 127.3, 126.4, 121.7, 116.8, 116.1, 113.5, 106.9.

Synthesis of $N^3$-methyl-2,5-diphenyl-$N^4$-(pyridin-2-yl)thiophene-3,4-diamine

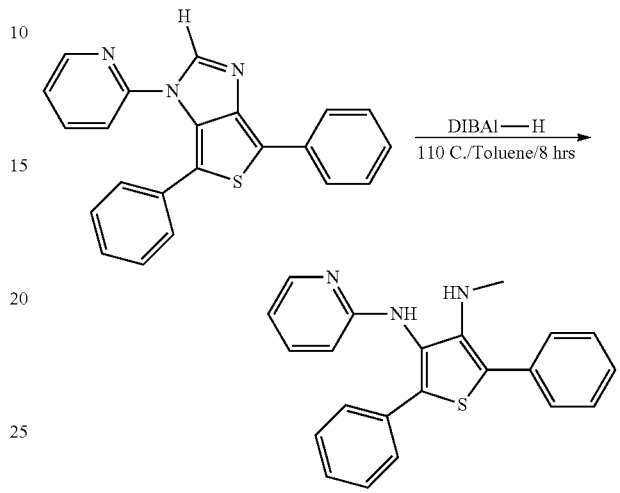

4,6-Diphenyl-1-(pyridin-2-yl)-1H-thieno[3,4-d]imidazole (1.0 g, 0.003 mol), was placed into a round bottom flask containing dry toluene (50 ml) and the reaction mixture was placed under a nitrogen atmosphere. DIBAL-H (10 ml in THF) was added portion wise via syringe, and once fully added the reaction mixture was heated at 100° C. over 16 hours. After this time water (1.0 ml) was added and the solution left to stir for 10 minutes. A further 50 ml was then added drop wise over 30 minutes. The solution was then diluted with dichloromethane (1.0 L), transferred to a separatory funnel, washed (3×250 ml water), the organic phase was then separated, dried (MgSO₄), filtered and solvent removed to give 1.0 g crude viscous yellow solid which was purified further by chromatography (100% petroleum spirits (BP 40-60° C.) to 1:1 petrol/EtOAc gradient elution) to give 0.8 g (79%) of the diamino product. $H^1$-NMR (CDCl₃, 400 MHz): 8.63 (s, 1H), 8.63 (br-s, 1H), 8.09 (d, 1H), 7.62 (d, 2H), 7.50 (d, 2H), 7.41 (m, 3H), 7.25 (m, 4H), 6.67 (m, 2H), 6.42 (d, 1H), 2.58 (s, 3H). $C^{13}$-NMR (CDCl₃, 100 MHz): 151.4, 148.9, 148.2, 137.9, 133.9, 133.3, 132.6, 131.6, 129.5, 129.1, 128.2, 127.6, 127.3, 126.4, 121.7, 116.9, 30.2.

What is claimed is:
1. A compound of Formula 1 or Formula 2:

Formula 1

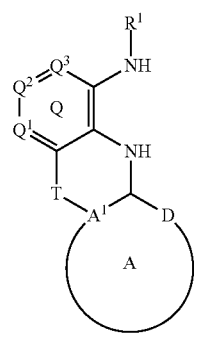

-continued

Formula 2

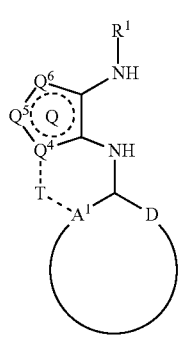

wherein
R$^1$ is selected from C$_{1-20}$alkyl, C$_{2-20}$alkenyl, C$_{2-20}$alkynyl, and a 5 or 6 membered aryl or heteroaryl, each of which is optionally substituted with one or more substituents each independently selected from halo, CN, NO$_2$, C(O)R$^2$, OR$^2$, OS(O)$_2$R$^2$, NR$^2$R$^3$, SR$^2$, aryl and heteroaryl; wherein R$^2$ and R$^3$ are each independently selected from hydrogen and C$_{1-6}$alkyl;

Q is an optionally substituted, optionally fused 5 or 6 membered heterocyclic ring, wherein the dashed circle indicates the optional location of up to two optional double bonds in the ring; and Q$^1$, Q$^2$ and Q$^3$, are each independently selected from CR$^4$ or N; wherein at least one of Q$^1$, Q$^2$ and Q$^3$ is N; and each R$^4$ is independently selected from hydrogen, halo, CN, NO$_2$, C(O)R$^2$, OR$^2$, OS(O)$_2$R$^2$, NR$^2$R$^3$, SR$^2$, optionally substituted C$_{1-20}$alkyl, optionally substituted C$_{2-20}$alkenyl, optionally substituted C$_{2-20}$alkynyl, and optionally substituted 5 or 6 membered aryl or heteroaryl, and optionally two R$^4$ substituents from adjacent ring atoms are joined together to form an optionally substituted 5 or 6 membered aryl or heteroaryl ring; wherein R$^2$ and R$^3$ are defined as above;

Q$^4$, Q$^5$ and Q$^6$, are each independently selected from N, S, O, CR$^4$ and NR$^5$, wherein at least one of Q$^4$, Q$^5$ and Q$^6$ is selected from N, S, O and NR$^5$; wherein R$^4$ is defined as above and R$^5$ is defined according to R$^1$ above; with the proviso that when T is present then Q$^4$ is selected from C-T and N-T, and when T is absent Q is not a furo[2,3-C]pyridine group;

T is a tether group between rings Q and A of 1 to 3 atoms in length linked together in a linear chain, wherein the dashed lines between Q$^4$ atom and A ring indicates T is an optional group, and wherein T is selected from C, N, O, S, Si and B, each of which is optionally substituted with one or more substituents independently selected from hydrogen, halo, CN, NO$_2$, =O, C(O)R$^2$, OR$^2$, OS(O)$_2$R$^2$, NR$^2$R$^3$, SR$^2$, optionally substituted C$_{1-10}$alkyl, optionally substituted C$_{2-10}$alkenyl, optionally substituted C$_{2-10}$alkynyl and optionally substituted 5 or 6 membered aryl or heteroaryl, and optionally fused with a 3-6 membered carbocycle or heterocycle; and wherein R$^2$ and R$^3$ are each independently defined as above, A is a monocyclic or bicyclic 5 or 6 membered heterocyclic ring containing a donor atom D and a ring atom A$^1$, and optionally having 1 or 2 additional ring heteroatoms selected from O, S and N, wherein the heterocyclic ring is optionally substituted with 1 to 3 substituents independently selected from hydrogen, halo, CN, NO$_2$, C(O)R$^2$, OR$^2$, OS(O)$_2$R$^2$, NR$^2$R$^3$, SR$^2$, optionally substituted C$_{1-20}$alkyl, optionally substituted C$_{2-20}$alkenyl, optionally substituted C$_{2-20}$alkynyl, and optionally substituted 5 or 6 membered aryl or heteroaryl; wherein R$^2$ and R$^3$ are each independently defined as above;

A$^1$ is selected from C, O, S, N, CR$^8$, C(R$^8$)$_2$ and NR$^9$; wherein each R$^8$ is independently selected from hydrogen, halo, CN, NO$_2$, C(O)R$^2$, OR$^2$, OS(O)$_2$R$^2$, NR$^2$R$^3$, SR$^2$, optionally substituted C$_{1-20}$alkyl, optionally substituted C$_{2-20}$alkenyl, optionally substituted C$_{2-20}$alkynyl, optionally substituted 5 or 6 membered aryl or heteroaryl; wherein R$^9$ is selected from hydrogen, C$_{1-20}$alkyl, C$_{2-20}$alkenyl, C$_{2-20}$alkynyl, and a 5 or 6 membered aryl or heteroaryl, each of which can be optionally substituted with one or more substituents independently selected from halo, CN, NO$_2$, C(O)R$^2$, OR$^2$, OS(O)$_2$R$^2$, NR$^2$R$^3$, SR$^2$, aryl and heteroaryl; and wherein R$^2$ and R$^3$ are defined as above; and D is a donor atom selected from N, O, S, P, Se and Te.

2. The compound of claim 1, wherein R$^1$ is selected from optionally substituted C$_{1-10}$alkyl and optionally substituted monocyclic 5 or 6 membered aryl or heteroaryl.

3. The compound of claim 1, wherein the compound is of Formula 1, wherein Q$^1$, Q$^2$ and Q$^3$ are each independently selected from CR$^4$ or N; and wherein at least one of Q$^1$, Q$^2$ and Q$^3$ is N.

4. The compound of claim 1, wherein the compound is of Formula 2, wherein when T is present, Q$^4$ is selected from C-T and N-T.

5. The compound of claim 1, wherein Q$^4$, Q$^5$ and Q$^6$, are each independently selected from N, S and CR$^4$, and at least one of Q$^4$, Q$^5$ and Q$^6$ is selected from N and S.

6. The compound of claim 5, wherein Q$^5$ is S and Q$^4$ and Q$^6$ are CR$^4$.

7. The compound of claim 1, which is selected from a compound of Formula 2, wherein when T is absent, Q$^4$, Q$^5$ and Q$^6$, are each independently selected from N, S, CR$^4$ and NR$^5$, wherein at least one of Q$^4$, Q$^5$ and Q$^6$ is selected from N, S and NR$^5$.

8. The compound of claim 1, wherein T is a tether group provided by a linear chain of 1 to 3 atoms in length independently selected from —N(R$^7$)—, —N(R$^7$)—C(=O)—, —O—, —O—C(=O)—, —C(=O)—, —S—, —S(=O)—, —S(=O)$_2$—, C$_{1-3}$alkyl and C$_{2-3}$alkenyl; wherein the C$_{1-3}$alkyl and C$_{2-3}$alkenyl are each optionally interrupted by a group selected from —N(R$^7$)—, —N(R$^7$)—C(=O)—, —O—, —O—C(=O)—, —C(=O)—, —S—, —S(=O)— and S(=O)$_2$, and optionally substituted with one or more substituents independently selected from halo, CN, NO$_2$, C(O)R$^2$, OR$^2$, OS(O)$_2$R$^2$, NR$^2$R$^3$, SR$^2$, C$_{1-10}$alkyl, C$_{2-10}$alkenyl, C$_{2-10}$alkynyl, C$_{1-10}$alkylhalo, C$_{2-10}$alkenylhalo and C$_{2-10}$alkynylhalo, and optionally fused with a 3-6 membered carbocycle or heterocycle; and wherein R$^7$ is selected from hydrogen and C$_{1-10}$alkyl.

9. The compound of claim 8, wherein T is the optionally substituted, optionally fused C$_{1-3}$alkyl.

10. The compound of claim 1, wherein A is an optionally substituted monocyclic or bicyclic 5 or 6 membered heteroaryl ring.

11. The compound of claim 1, wherein D is N.

12. The compound of claim 1, wherein A is an optionally substituted pyridine group.

13. A compound of Formula 3 or Formula 4:

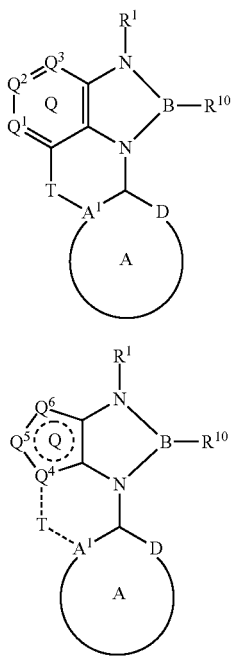

Formula 3

Formula 4 wherein

R$^1$ is selected from C$_{1-20}$alkyl, C$_{2-20}$alkenyl, C$_{2-20}$alkynyl, and a 5 or 6 membered aryl or heteroaryl, each of which is optionally substituted with one or more substituents each independently selected from halo, CN, NO$_2$, C(O)R$^2$, OR$^2$, OS(O)$_2$R$^2$, NR$^2$R$^3$, SR$^2$, aryl and heteroaryl; wherein R$^2$ and R$^3$ are each independently selected from hydrogen and C$_{1-6}$alkyl;

Q is an optionally substituted, optionally fused 5 or 6 membered heterocyclic ring, wherein the dashed circle indicates the optional location of up to two optional double bonds in the ring; and Q$^1$, Q$^2$ and Q$^3$, are each independently selected from CR$^4$ or N; wherein at least one of Q$^1$, Q$^2$ and Q$^3$ is N; and each R$^4$ is independently selected from hydrogen, halo, CN, NO$_2$, C(O)R$^2$, OR$^2$, OS(O)$_2$R$^2$, NR$^2$R$^3$, SR$^2$, optionally substituted C$_{1-20}$alkyl, optionally substituted C$_{2-20}$alkenyl, optionally substituted C$_{2-20}$alkynyl, and optionally substituted 5 or 6 membered aryl or heteroaryl, and optionally two R$^4$ substituents from adjacent ring atoms are joined together to form an optionally substituted 5 or 6 membered aryl or heteroaryl ring; wherein R$^2$ and R$^3$ are defined as above;

Q$^4$, Q$^5$ and Q$^6$, are each independently selected from N, S, O, CR$^4$ and NR$^5$, wherein at least one of Q$^4$, Q$^5$ and Q$^6$ is selected from N, S, O and NR$^5$; wherein R$^4$ is defined as above and R$^5$ is defined according to R$^1$ above; with the proviso that when T is present then Q$^4$ is selected from C-T and N-T, and when T is absent Q is not a furo[2,3-C]pyridine group;

T is a tether group between rings Q and A of 1 to 3 atoms in length linked together in a linear chain, wherein the dashed lines between Q$^4$ atom and A ring indicates T is an optional group, and wherein T is selected from C, N, O, S, Si and B, each of which is optionally substituted with one or more substituents independently selected from hydrogen, halo, CN, NO$_2$, =O, C(O)R$^2$, OR$^2$, OS(O)$_2$R$^2$, NR$^2$R$^3$, SR$^2$, optionally substituted C$_{1-10}$alkyl, optionally substituted C$_{2-10}$alkenyl, optionally substituted C$_{2-10}$alkynyl and optionally substituted 5 or 6 membered aryl or heteroaryl, and optionally fused with a 3-6 membered carbocycle or heterocycle; and wherein R$^2$ and R$^3$ are each independently defined as above, A is a monocyclic or bicyclic 5 or 6 membered heterocyclic ring containing a donor atom D and a ring atom A$^1$, and optionally having 1 or 2 additional ring heteroatoms selected from O, S and N, wherein the heterocyclic ring is optionally substituted with 1 to 3 substituents independently selected from hydrogen, halo, CN, NO$_2$, C(O)R$^2$, OR$^2$, OS(O)$_2$R$^2$, NR$^2$R$^3$, SR$^2$, optionally substituted C$_{1-20}$alkyl, optionally substituted C$_{2-20}$alkenyl, optionally substituted C$_{2-20}$alkynyl, and optionally substituted 5 or 6 membered aryl or heteroaryl; wherein R$^2$ and R$^3$ are each independently defined as above;

A$^1$ is selected from C, O, S, N, CR$^8$, C(R$^8$)$_2$ and NR$^9$; wherein each R$^8$ is independently selected from hydrogen, halo, CN, NO$_2$, C(O)R$^2$, OR$^2$, OS(O)$_2$R$^2$, NR$^2$R$^3$, SR$^2$, optionally substituted C$_{1-20}$alkyl, optionally substituted C$_{2-20}$alkenyl, optionally substituted C$_{2-20}$alkynyl, optionally substituted 5 or 6 membered aryl or heteroaryl; wherein R$^9$ is selected from hydrogen, C$_{1-20}$alkyl, C$_{2-20}$alkenyl, C$_{2-20}$alkynyl, and a 5 or 6 membered aryl or heteroaryl, each of which can be optionally substituted with one or more substituents independently selected from halo, CN, NO$_2$, C(O)R$^2$, OR$^2$, OS(O)$_2$R$^2$, NR$^2$R$^3$, SR$^2$, aryl and heteroaryl; and wherein R$^2$ and R$^3$ are defined as above;

D is a donor atom selected from N, O, S, P, Se and Te; and

R$^{10}$ is selected from hydrogen and halo.

14. A metal complex of Formula 5 or Formula 6:

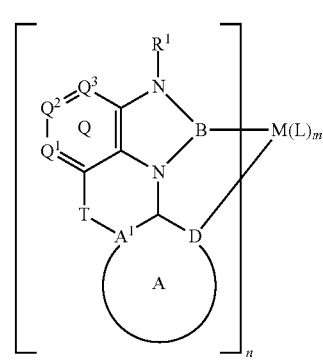

Formula 5

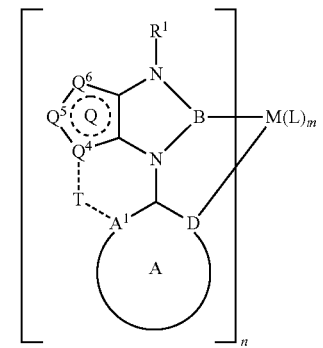

Formula 6 wherein

M is a metal atom selected from Ir, Pt, Rh, Pd, Ru and Os;

n is an integer selected from 1, 2 and 3;

m is an integer selected from 0, 1, 2, 3, 4, and 5;

L is a monodentate or bidentate ligand; and $R^1$ is selected from $C_{1-20}$alkyl, $C_{2-20}$alkenyl, $C_{2-20}$alkynyl, and a 5 or 6 membered aryl or heteroaryl, each of which is optionally substituted with one or more substituents each independently selected from halo, CN, $NO_2$, $C(O)R^2$, $OR^2$, $OS(O)_2R^2$, $NR^2R^3$, $SR^2$, aryl and heteroaryl; wherein $R^2$ and $R^3$ are each independently selected from hydrogen and $C_{1-6}$alkyl;

Q is an optionally substituted, optionally fused 5 or 6 membered heterocyclic ring, wherein the dashed circle indicates the optional location of up to two optional double bonds in the ring; and $Q^1$, $Q^2$ and $Q^3$, are each independently selected from $CR^4$ or N; wherein at least one of $Q^1$, $Q^2$ and $Q^3$ is N; and $R^4$ is independently selected from hydrogen, halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, optionally substituted 5 or 6 membered aryl or heteroaryl, and optionally two $R^4$ substituents from adjacent ring atoms are joined together to form an optionally substituted 5 or 6 membered aryl or heteroaryl ring; wherein $R^2$ and $R^3$ are defined as above;

$Q^4$, $Q^5$ and $Q^6$, are each independently selected from N, S, O, $CR^4$ and $NR^5$, wherein at least one of $Q^4$, $Q^5$ and $Q^6$ is selected from N, S, O and $NR^5$; wherein $R^4$ is defined as above and $R^5$ is defined according to $R^1$ above; with the proviso that when T is present then $Q^4$ is selected from C-T and N-T, and when T is absent Q is not a furo[2,3-C]pyridine group;

T is a tether group between rings Q and A of 1 to 3 atoms in length linked together in a linear chain, wherein the dashed lines between $Q^4$ atom and A ring indicates T is an optional group, and wherein T is selected from C, N, O, S, Si and B, each of which is optionally substituted with one or more substituents independently selected from hydrogen, halo, CN, $NO_2$, =O, $C(O)R^2$, $OR^2$, $OS(O)_2R^2$, $NR^2R^3$, $SR^2$, optionally substituted $C_{1-10}$alkyl, optionally substituted $C_{2-10}$alkenyl, optionally substituted $C_{2-10}$alkynyl and optionally substituted 5 or 6 membered aryl or heteroaryl, and optionally fused with a 3-6 membered carbocycle or heterocycle; and wherein $R^2$ and $R^3$ are each independently defined as above, A is a monocyclic or bicyclic 5 or 6 membered heterocyclic ring containing a donor atom D and a ring atom $A^1$, and optionally having 1 or 2 additional ring heteroatoms selected from O, S and N, wherein the heterocyclic ring is optionally substituted with 1 to 3 substituents independently selected from hydrogen, halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, and optionally substituted 5 or 6 membered aryl or heteroaryl; wherein $R^2$ and $R^3$ are each independently defined as above;

$A^1$ is selected from C, O, S, N, $CR^8$, $C(R^8)_2$ and $NR^9$; wherein each $R^8$ is independently selected from hydrogen, halo, CN, $NO_2$, $C(O)R^2$, $OR^2$, $OS(O)_2R^2$, $NR^2R^3$, $SR^2$, optionally substituted $C_{1-20}$alkyl, optionally substituted $C_{2-20}$alkenyl, optionally substituted $C_{2-20}$alkynyl, optionally substituted 5 or 6 membered aryl or heteroaryl; wherein $R^9$ is selected from hydrogen, $C_{1-20}$alkyl, $C_{2-20}$alkenyl, $C_{2-20}$alkynyl, and a 5 or 6 membered aryl or heteroaryl, each of which can be optionally substituted with one or more substituents independently selected from halo, CN, $NO_2$, $C(O)R^2$, $OR^2$, $OS(O)_2R^2$, $NR^2R^3$, $SR^2$, aryl and heteroaryl; and wherein $R^2$ and $R^3$ are defined as above; and D is a donor atom selected from N, O, S, P, Se and Te.

15. The metal complex of claim 14, wherein M is Ir.

16. The metal complex of claim 14, wherein n is 3, m is 0 and L is absent.

17. The metal complex of claim 14, wherein the metal complex is of Formula 5.

18. The metal complex of claim 14, wherein the metal complex is of Formula 6.

19. An emission material comprising a metal complex of Formula 5 or Formula 6 as defined in claim 14.

20. An organic electroluminescent device comprising at least one pair of electrodes comprising a cathode and an anode; and at least one layer comprising the emission material as defined in claim 19 that is arranged between the at least one pair of electrodes.

* * * * *